United States Patent [19]

Colman et al.

[11] Patent Number: 5,614,194

[45] Date of Patent: Mar. 25, 1997

[54] PROTECTIVE PEPTIDE ANTIGEN

[75] Inventors: David R. Colman; Joan Ellis; G. Nigel Godson; Ruth S. Nussenzweig; Victor N. Nussenzweig; Pamela S. Svec; Fidel Zavala, all of New York, N.Y.

[73] Assignee: New York University, New York, N.Y.

[21] Appl. No.: 461,945

[22] Filed: Jun. 5, 1995

Related U.S. Application Data

[63] Continuation of Ser. No. 32,731, Mar. 16, 1993, abandoned, which is a continuation of Ser. No. 864,172, Apr. 3, 1992, abandoned, which is a continuation of Ser. No. 99,652, Sep. 21, 1987, abandoned, which is a continuation of Ser. No. 574,553, Jan. 27, 1984, abandoned, which is a continuation-in-part of Ser. No. 234,096, Feb. 12, 1981, Pat. No. 4,466,917.

[30] Foreign Application Priority Data

Jan. 28, 1983 [GB] United Kingdom ............... 8302349

[51] Int. Cl.$^6$ .......................... C12N 15/00; A61K 39/00; C07K 14/00; C07K 5/00
[52] U.S. Cl. ........................ 424/191.1; 424/185.1; 530/350; 530/327; 530/328; 435/172.3
[58] Field of Search ........................ 435/172.3; 350/328; 350/327; 424/88

[56] References Cited

U.S. PATENT DOCUMENTS 4,466,917  8/1984  Nussenzweig et al. ............. 435/172.3
4,769,235  9/1988  Schlessinger ............................ 424/88

OTHER PUBLICATIONS

Schmidt, L,H 1982 Am. J. Trop. Med. Hyg. 31(3):612–645.
Goman, M et al 1982 Mol. Biochem. Parasitol. 5:391–400 and *Abstract* J. Cell. Biochem. Suppl., 1983.
Zavala, F et al Oct. 1982 Nature 299:737–738.
Cochrane et al Sep. 1982 Proc. Natl. Acad. Sci. 79:5651–5655.
Nardin, E et al Jul. 1982 J. Exp. Med. 156:20–30.
Yoshida et al Oct. 1981 J. Exp. Med. 154:1225–1236.
Hopp, T et al. Jun. 1981 Proc. Natl. Acad. Sci. 78:3824–3828.
Kilejian, A. 1980 Am. J. Trop. Med. Hyg. 29(5):1125–1128.
Nussenzweig Sep. 1969 Military Medicine 10(special issue):1176–1182.
Yoshida et al, Science vol, 207 pp. 71–73 Jan. 4, 1980.
Perrin et al, Nature vol. 289 pp. 301–303 Jan. 22, 1981.
Potocnjak et al, J. Exp. Med. vol. 151 pp. 1504–1513 Jun. 1980.
Nardin et al, J. Exp. Med. vol. 156 pp. 20–30 Jul. 1982.
Godson et al. 1983. Nature 305:29–33.
Goman et al. Mol. Biochem. Parasitology 5:391. 1982.
Potocnjak et al J Exp Med 151:1504. 1986.
Perrin et al Nature 289:301. 1981.
Nardin et al J. Exp. Med 156:20. 1982.
Lupski et al, Science vol. 220 pp. 1285–1288 Jun. 17, 1983.
Godson et al, Nature vol. 305 pp. 29–33 Sep. 1, 1983.
Yoshida et al, Science vol. 207 pp. 71–73 Jan. 4, 1980.
Blochey et al JBC 255(13):6284, 1980 (Jul.).

*Primary Examiner*—Suzanne E. Ziska
*Attorney, Agent, or Firm*—Darby & Darby, PC

[57] ABSTRACT

Described is a antigen and antigenic amino acid sequence consisting of repeating units of the immunodominant epitope region of the circumsporozoite surface protein of a parasite of the genus Plasmodium. Also described is a related fusion protein produced by a recombinant microorganism and a vaccine for immunizing mammals against malaria.

17 Claims, 8 Drawing Sheets

FIG. 1

PROTECTIVE PEPTIDE ANTIGEN

The government has rights in the invention based upon research support in the form of Grant No. 5R01-Ail7429-03 from the Department of Health and Human Services and Grant No. AID-DPE-0453-C-00-2002-00 from the Department of State, Agency for International Development.

This is a continuation of application Ser. No. 08/032,731, filed Mar. 16, 1993, now abandoned; which is a continuation of application Ser. No. 07/864,172 filed Apr. 3, 1992, now abandoned; which is a continuation of application Ser. No. 07/099,652, filed Sep. 21, 1987, now abandoned; which is a continuation of application Ser. No. 06/574,553, filed Jan. 27, 1984, now abandoned; which is a continuation-in-part of application Ser. No. 06/234,096, filed Feb. 12, 1981, now issued as U.S. Pat. No. 4,466,917.

BACKGROUND OF THE INVENTION

The present invention relates to the field of antigens suitable for providing protective immunity against malaria when incorporated into a vaccine. Malaria constitutes a worldwide public health hazard of enormous economic and medical significance. The disease contributes substantially to infant mortality in endemic areas and remains a severe and debilitating illness for those who remain afflicted with it as adults. Despite advances in the techniques of mosquito abatement and improved public health measures, regions where the disease is considered endemic are increasing in area. Furthermore, the risk of infection has substantially increased in some parts of the world because of the occurrence of new drug-resistant strains of the malaria parasite.

The causative agent of malaria is a protozoan of the genus Plasmodium. Individual species within the genus appear to have a restricted host range for the animals they infect. For example, *P. berghei* and *P. yoeli* are infective to rodents, *P. knowlesi* and *P. cynomolgi* are primarily infective to monkeys, while *P. falciparum, P. vivax, P. ovale* nd *P. malariae* are the species primarily infective to humans. Despite species differences in host range, the life cycles, mode of infection, biochemistry and genetics of the various Plasmodium species are markedly similar.

The life cycle of Plasmodium is complex, the organism undergoing several distinct morphological changes, involving the participation of a mammalian host and a mosquito vector. The parasite, in the sporozoite form, is introduced to the mammalian host through the bite of the mosquito vector. The sporozoites rapidly disappear from the blood stream and are next found as intracellular parasites of liver parenchymal cells. A blood infection ensues, characterized by the well-known clinical symptoms of malaria after a complex series of morphological and biochemical transitions. The parasite is then found in the red blood cells, where it continues its development. Substantial amounts of the parasite may be obtained from the red blood cells of infected patients.

Vaccine development, to provide protective immunity against malaria infection has been thwarted by the fact that the parasite's life cycle in the mammalian host is primarily intracellular. Except for brief periods of time, the parasite is protected from contact with the immune system. Two stages in the parasite's life cycle during which it becomes briefly exposed to the immune system are, 1) the interval following initial infection before sporozoites have successfully invaded the cells of the liver and 2) the interval during which merozoites leave infected red blood cells and enter uninfected red blood cells. The transient exposure of the merozoite forms in the extracellular milieu has provided the basis for prior art attempts to develop host immunity to blood forms of the parasite. European published Patent Application, Number 62924, discloses antigenic proteins useful in the making of a vaccine to provide immunity against merozoite forms of the parasite. The utility of such a vaccine would presumably lie in limiting or arresting the course of the established malaria infection.

An alternative approach, based upon sporozoite antigens has led to the discovery of antigenic and immunogenic proteins of sporozoites that are capable of providing protective immunity against initial infection, when administered as a vaccine, Cochrane, A. H., et al., in *Malaria*, vol. 3, (J. Kreier, ed.) Academic Press N.Y. (1980) pp. 163–202; Nussenzweig, R. S. in *Immunity to Blood Parasites of Animals and Man*, (L. Miller, J. Pino and J. McKelvey, eds.) Plenum, N.Y. (1977) pp. 75–87. Gwadz, R. W., et al., Bull, W. H. O. Suppl. 1, 57, 165 (1979); Clyde, D. F., et al., Am. J. Trop, Med. and Hyg. 24, 397 (1975); McCarthy, V., et al., Exp. Parasitol. 41, 167 (1977).

These proteins are antigenically distinguishable for each Plasmodium species, but have numerous structural properties in common including chromatographic behavior, isoelectric point, and electrophoretic mobility. The sporozoite antigens range in molecular weight from approximately 40,000 daltons to 70,000 daltons and have low isoelectric points, Santoro, F. et al., J. Biol. Chem. 258, 3341, 1983.

The comparison of tryptic digests of purified sporozoite antigen proteins of different Plasmodium species shows that several tryptic peptides have identical retention times on reverse-phase high performance liquid chromatography, indicating that there is a high degree of homology between antigenic proteins of different species.

The sporozoite antigens are components of the sporozoite surface coat. The presence of the sporozoite antigens is indicated by a characteristic immunologic reaction known as the circum-sporozoite reaction, and by immunofluorescence tests. See Vanderberg, J. P., et al, Mil. Med. (Suppl.) 134, 1183 (1969); and Nardin, E., et al, Nature 274, 55 (1978).

These reactions make it possible to specifically detect the sporozoite antigen for a given Plasmodium species, without resorting to time-consuming in vivo tests. This, in turn, has made it possible to develop specific radioimmunoassays for sporozoite antigens, and ultimately for the production of malaria antibodies directed against sporozoite antigens of Plasmodium species.

Antibodies against the sporozoite antigens have been shown to provide protective immunity against the Plasmodium species from which they were derived, in rodents, monkeys and in human volunteers. The sporozoite protective antigen protein is herein termed CS protein, circumsporozoite protein, or sporozoite CS protein, these terms being deemed equivalent. A co-pending U.S. application, Ser. No. 234,096, filed Feb. 12, 1981, has been filed, disclosing a vaccine based upon purified CS protein. Said application (a copy of which is annexed hereto as Appendix A) is incorporated herein by reference as though set forth in full.

The results disclosed herein are based in part on the techniques and concepts of the field of immunology. For convenience, certain terms commonly used in the art are defined herein. The term "immunochemical reaction" is used to denote the specific interaction which occurs between an antigen and its corresponding antibody, regardless of the method of measurement. Such a reaction is characterized by a non-covalent binding of one or more antibody molecules to one or more antigen molecules. The immunochemical reaction may be detected by a large variety of immunoassays known in the art. The terms "immunogenic" or "antigenic" will be used here to describe the capacity of a given substance to stimulate the production of antibodies specifically immunoreactive to that substance when that substance is administered to a suitable test animal under conditions known to elicit antibody production. The term "protective antigen" refers to the ability of a given immunogen to confer resistance in a suitable host, against a given pathogen. The term "epitope", refers to a specific antibody binding site on an antigen. Macromolecular antigens such as proteins typically have several epitopes with distinctive antibody binding specificities. Different epitopes of the same antigen are distinguishable with the aid of monoclonal antibodies which, due to their high degree of specificity, are directed against single epitopes. Two different monoclonal antibodies directed against different epitopes on the same antigen may each bind the antigen without interfering with the other, unless the epitopes are so close together that the binding of one sterically inhibits the binding of the other. The term "immunodominant region" denotes an area of the antigen molecule which is mainly responsible for its antigenicity.

BRIEF DESCRIPTION OF THE DRAWINGS

FIG. 1 is the nucleotide and amino acid sequence of a β galactosidase fusion protein containing P. knowlesi CS protein immunogenic region.

SUMMARY OF THE INVENTION

Figure 2A:
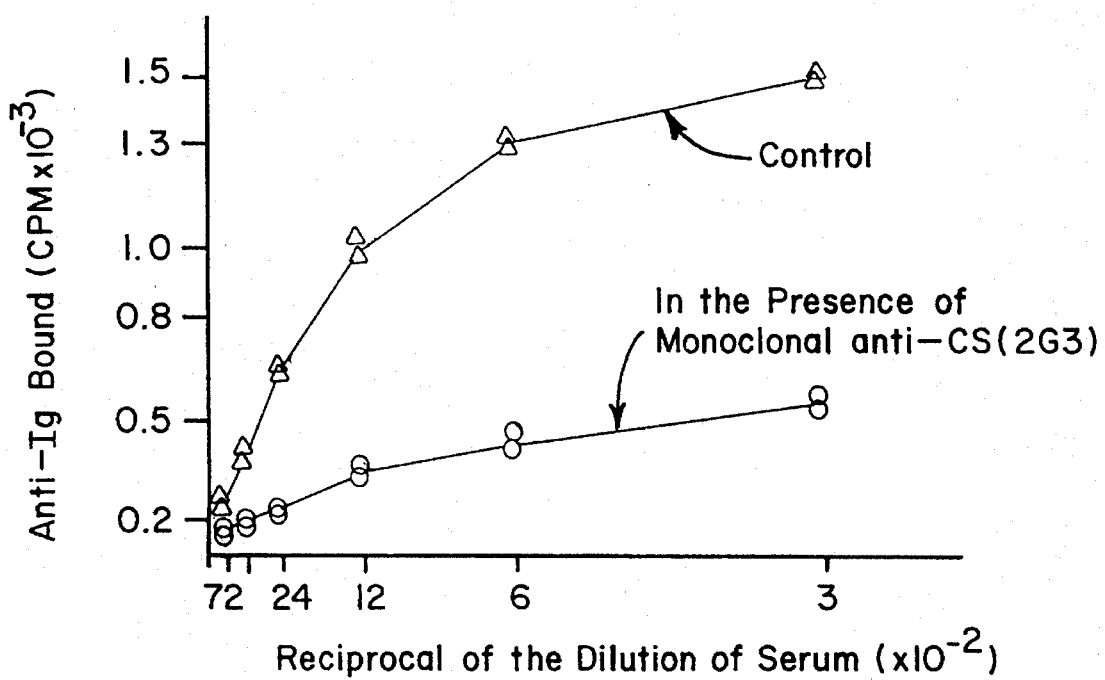
FIG. 2A is a plot showing the inhibitory effect of a monoclonal antibody to a CS protein (monoclonal anti-CS(2G3)) on the binding of polyclonal antibodies to sporozoite extracts.

The present invention is based on the discovery that the protective CS sporozoite antigens of the genus Plasmodium possess a single immunodominant region composed of repetitions of the same epitope. For P. knowlesi, the epitope has been shown to be a dodecapeptide whose sequence is repeated several times within the structure of the CS protein. The repeated peptide has been chemically synthesized in both monomeric and dimeric forms. The synthetic repeated peptide is immunochemically reactive with polyclonal antibody preparations against P. knowlesi. In addition, all monoclonal antibodies against CS proteins which neutralize the infectivity of sporozoites in vitro, also react with the synthetic peptide. Therefore, the synthetic repeated peptide constitutes substantially all of the immunogenic activity displayed by the naturally occurring sporozoite protective antigen of P. knowlesi.

Several lines of evidence indicate that CS proteins of the Plasmodium species infective to rodents, monkeys and humans are structurally similar. All possess an immunodominant region composed of similarly repeated epitopes. For each species, the repeated peptide of the sporozoite CS protein can be synthesized. The repeated peptide of a CS protein is immunogenic when administered in a composition, and by administration methods, known in the art to yield antibody production. On the basis of the discoveries and teachings herein described, structural determination and synthesis of the repeated peptide corresponding to any Plasmodium species sporozoite, and the preparation of a vaccine composition incorporating said peptide and capable of eliciting protective immunity against said species is now available to those of ordinary skill in the art.

As further confirmation of the close relationship of CS proteins of different Plasmodium species, monoclonal antibodies against P. knowlesi sporozoites have been shown to cross-react with P. falciparum antigen, a species infective to humans. It is therefore apparent that the development of other synthetic peptides more specifically reactive with human malaria species are well within the grasp of those ordinarily skilled in the art, following the teachings and disclosures as set forth herein.

DETAILED DESCRIPTION OF THE INVENTION

In the following description, the materials employed were commercially available, unless otherwise specified. Enzymes used in the cloning procedures were obtained from commercial sources. Restriction endonuclease reactions were carried out according to the manufacturer's instructions. Unless otherwise specified, the reaction conditions for other enzyme reactions were standard conditions used in the art, as described, for example, in Methods in Enzymology, volume 60 (R. Wu, Ed.) Academic Press, (1980). Unless otherwise specified, the abbreviations herein are standard abbreviations acceptable for publication in scientific journals normally used by those skilled in the art to publish their results, such those cited herein.

In general outline, the experiments and conclusions following from the results thereof are set forth. The approach taken herein to clone a DNA segment coding for the sporozoite antigen protein was to clone cDNA made from mRNA obtained from infected mosquitoes. The cDNA approach was preferred in the initial cloning work because it was not known whether Plasmodium genomic DNA contained introns that might prevent the expression of antigenically identifiable sporozoite proteins. Now that the short and repeated nature of the epitope is known, it is feasible to select for DNA encoding the epitopes from a library of genomic Plasmodium DNA. The initial experiments were performed with cDNA from mRNA of infected mosquitoes, since it was only at that stage that the Plasmodium was known to express the sporozoite antigen. A cDNA library was constructed from Poly (A)⁺RNA derived from *P. knowlesi*-infected mosquitoes. Double stranded cDNA, tailed with poly-C residues, were inserted into the plasmid pBR322, previously cut with Pst I and tailed with poly-G. Host cells transformed to tetracycline resistance were selected and single colonies of transformed cells were stored in microtiter dishes at −70° C.

The cDNA clones were screened for the ability to express a protein that contained the immunochemically reactive region of the sporozoite surface antigen. Once a cDNA coding for the sporozoite antigen was identified, others could readily be detected by hybridization using the originally cloned cDNA as a probe. Clones derived either from cDNA or genomic DNA libraries could be identified in this manner, based upon the homology between DNA segments coding for the sporozoite antigen of different Plasmodium species. Identification of clones expressing an immunoreactive protein was done by screening lysates of colonies of cells transformed (as above) with the cloned cDNA. Pools of 48 colonies were screened using a sensitive, two-site immunoradiometric assay performed with monoclonal antibodies. This permitted the detection of the CS protein in the transformed cells.

In short, a monoclonal antibody to *P. knowlesi* CS protein was adsorbed to the wells of a microtiter plate. Lysates from pools of 48 colonies were each added to the wells and incubated for sufficient time to allow the immunoreactive protein present in the lysate to bind to the adsorbed monoclonal antibody. The wells were then washed to remove any contaminating protein and a radio-labelled second monoclonal antibody to *P. knowlesi* CS protein was added. The labelled second monoclonal antibody attaches to the antigenic protein that is already bound to the surface of the microtitre well by the first monoclonal antibody. If a pool of 48 colonies was found to be positive, the colonies were screened individually in the same fashion. In this manner, positive clones were identified.

Figure 1:
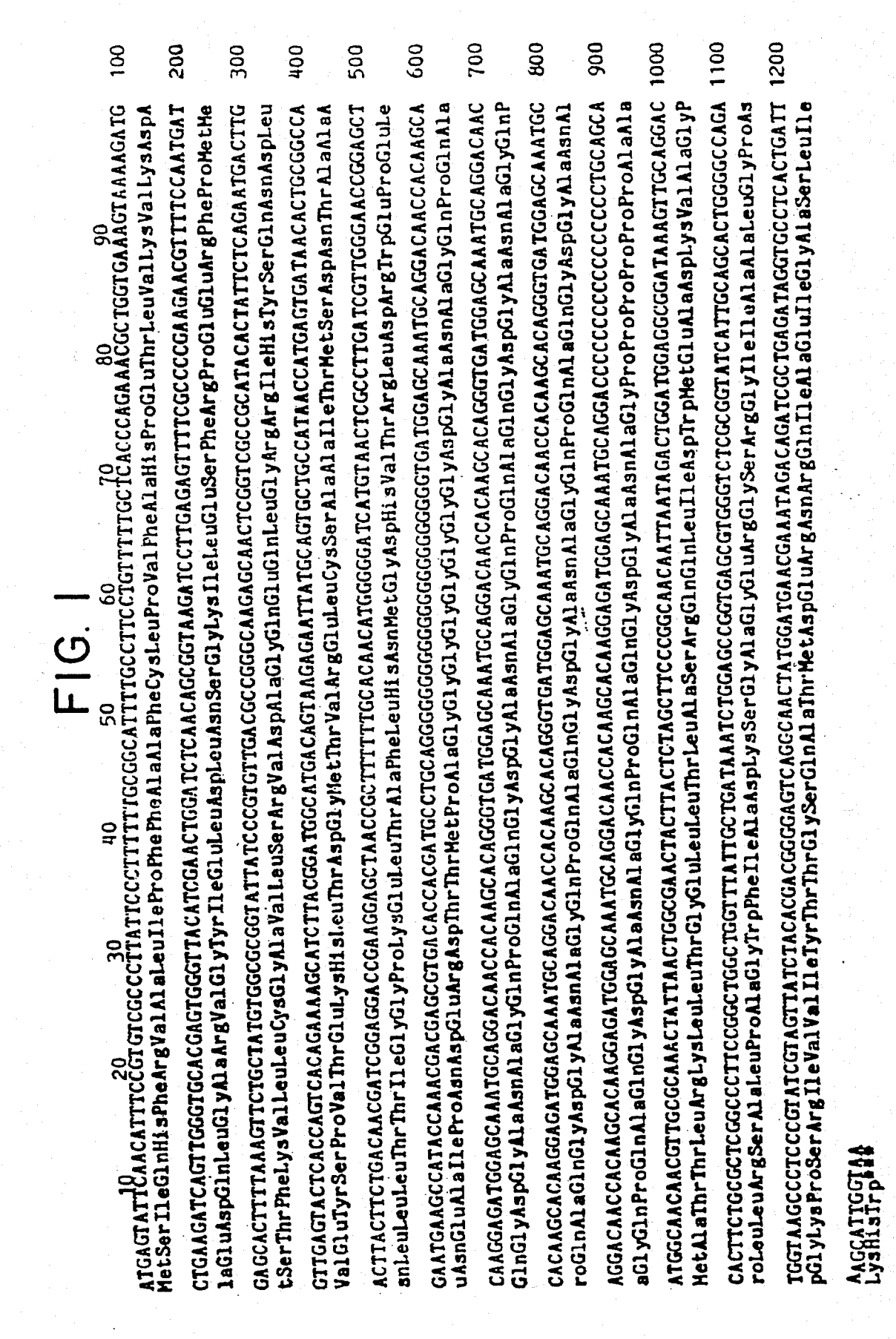

Whenever an immunoreactive clone was detected, plasmid DNA was isolated from it and used to transform another host cell strain, such as *E. coli* HB 101 or *E. coli* RR1. Transformants detected by tetracycline resistance were rechecked for the ability to express the immunochemically reactive protein, in order to confirm that the expression was a property of the plasmid DNA clone containing CS nucleotide sequences. Once suitable plasmid DNA was obtained from the positive clones, the nucleotide sequence of the cDNA insert coding for at least the immunoreactive region of the CS protein was obtained (by cloning onto M13). Methods of nucleotide sequence analysis are well known in the art, including the method of Maxam and Gilbert, W. Proc. Nat. Acad. Sci. USA 74, 560 (1977) and the method of Sanger, F. et al, Proc. Nat. Acad. Sci. USA 74, 5463 (1977). The latter method was employed in the present work. The complete nucleotide sequence of a segment of the *P. knowlesi* CS protein gene that contains the immunochemically reactive site is shown in FIG. 1.

A surprising feature of the nucleotide sequence was that it was repetitive. In *P. knowlesi* the sequence consisted of a 36 base pair repeat, 8 complete units of which were represented in one clone (24-mer) together with partial units at either end. In order to deduce the amino acid sequence coded by the DNA, it was necessary to identify the coding strand and, within the strand, the correct reading frame. In this context, 5 the advantage of using the Sanger and Coulson, supra sequencing method becomes evident. A sequencing vector, bacteriophage M13mp9, contains a betagalactosidase gene with a Pst I site in the same reading frame as the Pst I cleavage site of pBR322. Therefore, the reading frame can be deduced once the number of deoxy C-residues added during the tailing reaction is known and the sequencing vector can express a beta-galactosidase fusion protein comprising the immunochemically reactive part of the CS protein. Therefore, two different M13mp9 recombinants were obtained, with the 368 bp *P. knowlesi* DNA fragment inserted in opposite orientations. Only one of the two recombinants produced immunochemically reactive betagalactosidase fusion protein, as measured by the above-described radioimmunoassays. The clone producing the immunoreactive protein was used to identify the coding strand and direction of transcription of the *P. knowlesi* gene fragment.

The correct reading frame was also deduced using immunological procedures. These showed that the epitope defined by the monoclonal antibodies was destroyed by elastase, but not by trypsin nor by reducing agents, indicating that the epitope did not contain any of lysine, arginine or disulfide bonds, but might contain alanine residues.

On the basis of such experiments, the amino acid sequence of the 12 amino acid-containing repetitive peptide was deduced to be:

$$H_2N\text{-GlnAlaGlnGlyAspGlyAlaAsnAlaGlyGlnPro-COOH.}$$

To confirm the deduced amino acid sequence and immuno-chemical reactivity of the above-described sequence, a dodecapeptide of the same amino acid sequence and a dimer thereof were synthesized using an automated solid phase peptide synthesis system.

The monomer and dimer synthetic peptides were separately tested for immunochemical activity in the same type of radioimmunoassay as was used initially to screen the cDNA library. In this test, two antibody binding sites must be present in the antigen, one for binding to the first monoclonal attached to the microtiter well and the second for binding the added labelled antibody. Although the monomer peptide did not bind the labeled antibody, the dimer peptide was reactive, indicating that the dimer contained two complete, or nearly complete, antibody binding sites. Furthermore, the same assay showed that the monomer was able to compete with and specifically inhibit the binding of CS proteins of *P. knowlesi* to the microtiter wells bearing the first monoclonal antibody. Therefore, the sequence shown above contains an epitope of the sporozoite antigen. Another important observation was that all monoclonal antibodies to *P. knowlesi* obtained to date, as well as all polyclonal antibodies obtained from monkeys immunized with irradiated sporozoites, also reacted with the synthetic peptides. Actually, more than 70% of the antibodies to sporozoites, found in the serum of the immunized monkeys, recognized this single epitope (Zavala, et al., J. Exp. Med. 157:1947, 1983).

Therefore a chemically synthesized dodecapeptide having an amino acid sequence identical to that repeated in a sporozoite membrane protein contains substantially all of the antigenicity of the naturally occurring CS protein. It follows that based upon the principles of immunology and following techniques and procedures known to those of ordinary skill in the art, a synthetic peptide based upon the known amino acid sequence of a sporozoite CS protein can be incorporated into a vaccine composition capable of providing protective immunity in a host organism susceptible to a Plasmodium species from which, the sequence of the peptide was derived. The following experiments, generally described, demonstrate the essential structural and functional similarities between the sporozoite CS proteins of the Plasmodium species infective to rodents, monkeys and humans. These similarities are exploitable to identify and synthesize the antigenic peptides specific for any Plasmodium species including, in particular, those infective to humans. The structural determination and synthesis of the repeated peptide for any Plasmodium species can be carried out by methods described herein or by equivalent methods known in the art, or by methods known in the art which exploit the disclosures and teachings of the present invention to eliminate some of the more time-consuming and tedious aspects of the original experiments. Of significance is that cross reactivity has been observed between monoclonal antibodies to the CS proteins of different Plasmodium species. For example, antibodies to the CS protein of *P. knowlesi* cross react with the CS protein of *P. cynomolgi* and *P. falciparum*; antibodies to the CS protein of *P. cynomolgi* cross react with the sporozoite antigen of *P. vivax*; antibodies to the CS protein of *P. yoeli* nigeriensis cross react with sporozoite antigen of *P. berghei*, and in that instance, completely neutralize the infectivity of sporozoites of the latter species, for mice.

Additional immunochemical evidence has been adduced to demonstrate that all sporozoite CS proteins have a single immunodominant region and repetitive epitopes Zavala, et al., supra. The binding of several different monoclonal antibodies directed against the same sporozoite CS protein was tested, measuring the inhibitory effects that the binding of one might have on the other. Monoclonal antibodies directed against different sequences within an antigen should not interfere with their respective binding capacities. Conversely, if monoclonals are directed against the same epitope, or epitopes which are topographically close, they inhibit each other. In the case of *P. knowlesi*, every one of the six monoclonals used, strongly inhibited the binding of the others to the antigen.

The same experiments were performed using monoclonals to the sporozoite antigen proteins of *P. vivax, P. falciparum, P. malariae P. cynomolgi* and *P. berghei*, with identical results. Therefore, these sporozoite CS proteins all are characterized by having a single immunodominant region.

Of direct relevance to the development of a vaccine against human malaria is the observation that antibodies in the serum of humans vaccinated and protected against sporozoites of *P. falciparum* or *P. vivax* are also directed against the same immuno-dominant region of the sporozoite CS protein. Pretreatment of a crude extract of sporozoites of either species with a single monoclonal antibody directed against the sporozoite antigen of the same species almost completely inhibited the subsequent binding of the antigen (in the sporozoite extract) to polyclonal antibodies isolated from the serum of the vaccinated human volunteers (Zavala, et al., supra).

The fact that immunodominant regions of the CS proteins contain repetitive epitopes was demonstrated by a solid phase two site radioimmunoassay. In the assay, a monoclonal antibody was bound to the plastic surface a microtiter well, antigen was added and the antigen was found to the immobilized antibody. The well was then washed to remove any unbound material and a second monoclonal antibody, presumably directed against a different epitope of the same antigen, was added. The second antibody is labelled with a radioisotope to quantitate the binding of the second antibody. Binding of the second antibody is proportional to the amount of antigen bound in the well. This immunoassay can be performed only if the antigen contains at least two epitopes. The first epitope binds to the antibody immobilized to the plastic of the plate, the second binds the radiolabelled antibody. Surprisingly, in the case of every CS protein, the two site radioimmunoassay could be performed using a single monoclonal antibody. That is to say, the assay could be performed using unlabelled monoclonal antibody A as the first monoclonal and the same monoclonal A as the second monoclonal. The result demonstrates that the sporozoite CS protein has at least two identical epitopes.

A control experiment demonstrated that the result was not an artifact caused by aggregation of the sporozoite antigen protein. Extracts of *P. knowlesi* sporozoites were dissolved in 2.0% (w/v) sodium dodecylsulfate and 6M urea and fractionated by ultracentrifugation in sucrose gradients. The existence of two epitopes was demonstrated in fractions of the gradient containing proteins of molecular weight 40,000, corresponding to the size of a CS protein monomer. Furthermore, there was no indication of the presence of aggregates of CS proteins. Identical results were obtained in experiments performed with *P. vivax* and *P. falciparum* extracts (Zavala, et al, supra).

It is therefore clear that all sporozoite CS proteins have a single immunodominant region comprising a peptide repeated many times within the protein. The repeated peptide contains the epitope, and each sporozoite CS protein is composed of a plurality of such repeated peptide epitopes. These epitopes are very immunogenic in all animal species, including man. Synthetic peptides containing the epitope of a given sporozoite CS protein are functionally identical to naturally occurring sporozoite antigens, with the obvious exception of two site radioimmunoassays requiring two epitopes on the same molecule. The functional behavior in two site assays is reproduced by synthetic dimers of the repeated peptide.

It will be readily appreciated therefore that synthetic peptides, comprising an amino acid sequence corresponding to an epitope of a sporozoite CS protein in monomeric or multimeric form, can be incorporated into vaccines capable of inducing protective immunity against sporozoites of malaria parasites, e.g., *P. falciparum, P. vivax* and *P. malariae*. Techniques for enhancing the antigenicity of such repeated peptides include incorporation into a multimeric structure, binding to a highly immunogenic protein carrier, for example, keyhole limpet hemocyanin, or diptheria toxoid, and administration in combination with adjuvants or any other enhancers of immune response. Furthermore, it will be understood that peptides specific for a plurality of Plasmodium stages and species may be incorporated in the same vaccine composition to provide a multivalent vaccine. In addition, the vaccine composition may comprise antigens to provide immunity against other diseases in addition to malaria.

An amino acid sequence corresponding to an epitope of a CS protein (repeated peptide) may be obtained by chemical synthetic means or by purification from biological sources including genetically modified microorganisms or their culture media. The repeated peptide may be combined in an amino acid sequence with other peptides including fragments of other proteins, as for example, when synthesized as a fusion protein, or linked to other antigenic or non-antigenic peptides of synthetic or biological origin. The term "corresponding to an epitope of a CS protein" will be understood to include the practical possibility that, in some instances, amino acid sequence variations of a naturally occurring repeated peptide may be antigenic and confer protective immunity against malaria sporozoite infection. Possible sequence variations include, without limitation, amino acid substitutions, extensions, deletions, interpolations and combinations thereof. Such variations fall within the contemplated scope of the invention provided the peptide containing them is antigenic and antibodies elicited by such peptide cross-react with naturally occurring CS protein or non-variant repeated peptides of CS protein, to an extent sufficient to provide protective immunity when administered as a vaccine. Such vaccine compositions will be combined with a physiologically acceptable medium. Routes of administration, antigen dose, number and frequency of injections are all matters of optimization within the scope of ordinary skill in the art, particularly in view of the fact that there is experience in the art in providing protective immunity by the injection of inactivated sporozoites. It is anticipated that the principal value of providing immunity to sporozoite infection will be for those individuals who have had no previous exposure to malaria, e.g., infants and children who live in endemic and subendemic areas, and unexposed adults travelling into endemic areas. It is also anticipated that temporary immunity for infants may be provided by immunization of mothers during pregnancy. Details of the operation and practice of the present invention are set forth in the specific examples which follow.

EXAMPLE 1 cDNA clone coding for a sporozoite antigen protein.

The techniques of recombinant DNA technology make extensive use of enzyme-catalyzed reactions. Purified enzymes for use in the practice of the present invention are currently available from commercial sources. Commercially available enzymes and reagents were employed unless otherwise specified. Restriction endonucleases, their nomenclature and site specificities, have been described in detail by Roberts, R. J., Nucl. Acids Res., 8, p. 63 (1980). The restriction enzymes used in this work were used in amounts and under reaction conditions specified by the manufacturer for each enzyme.

Approximately 1000 *P. knowlesi* infected mosquitoes grown, maintained and collected as described by Cochrane et al., Proc. Natl. Acad. Sci. USA 79:5651–5655 (1982) were harvested and dissected to obtain thoracic segments which were stored on ice until the dissection was completed. RNA was prepared from the thoraxes essentially as described by Seeburg, P. H., et al; Cell, 12, 157 (1977), and by Chirgwin, J. M., et al; Biochemistry, 24, 5294 (1979). The tissue was homogenized in 10 ml of 5M guanidine thiocyanate, pH 5.0, 10 mM EDTA and 0.1M 2-mercaptoethanol until all the tissue was dispersed. The solution was centrifuged at 10,000 rpm for 10 minutes and the supernatant adjusted to 2% (w/v) Sarkosyl (Trademark, ICN Pharmaceuticals, Plainview, N.Y.), and heated at 65° C. for two minutes. Cesium chloride was then added (0.1 g/ml of solution) and the resulting solution was layered over 2 ml cushions of half-saturated CsCl in 10 mM EDTA in SW41 (Trademark, Beckman Instruments, Fullerton, Calif.) cellulose nitrate tubes. Centrifugation was at 28,000 rpm for approximately 20 hours at 20° C. The RNA pellet was dissolved in 5 mM EDTA, 0.5% (w/v) Sarkosyl and 5% (w/v) 2-mercaptoethanol, extracted with phenol and chloroform and precipitated with ethanol.

Usually, 0.5–1 mg of RNA were obtained per g of tissue. The RNA was then passed over an oligo (dT)-cellulose column (Aviv, H., et al, Proc. Nat. Acad. Sci. USA, 69, 1408 (1972), to enrich for the polyadenylated fraction. Alternatively, the RNA can be prepared from the mosquito thoraces by the procedure modified from Liu, C. P., et al., Proc. Nat. Acad. Sci. 76:4503, 1979. According to this procedure, tissue was homogenized in 8–10 vol. of 4M guanidine isothiocyanate pH 5.0 (with glacial acetic acid) and 0.1M 2-mercaptoethanol until the tissue was dispersed. Centrifugation took place at 9,000 rpm for 3 minutes, and the supernatant was layered over 0.2 vol. of 5.7M CsCl in 0.10M EDTA (pH 6.5) in SW 41 cellulose nitrate tubes. Centrifugation was at 35,000 rpm for 16–20 hours @ 20° C. Approximately 0.5–1 mg of RNA was obtained per gram of tissue. Poly(A)+RNA was then oligo-dT selected as described above.

A sample of mRNA isolated as described was translated in vitro using a translation system prepared from wheat germ (modified from Roberts, B. E., et al, Proc. Nat. Acad. Sci. USA, 70, 2330 (1973)). Proteins produced by in vitro translation were immunoprecipitated as described in Example 2, (alternatively, as disclosed by Goldman, B. M., and Blobel, G., Proc. Natl. Acad. Sci., 75:5066 (1978)) and fractionated on an SDS-polyacrylamide gel (SDS-Page) as described by Yoshida, et al, J. Exp. Med 154, 1225 (1981) and in Example 2 of copending U.S. application Ser. No. 234,096, incorporated herein by reference. mRNA fractions containing sequences coding for the CS-proteins can be identified by this means.

For preparative cDNA synthesis total polyadenylated mRNA (approximately 20 µg) was treated in 100 µl volume with 1 mM methyl mercury (hereinafter MeHg) (Aldrich Chemical, Milwaukee, Wis.) at room temperature for 5 minutes. The treatment was stopped by adding 0.5% (0.5µl per 100 µl) of undiluted β-mercaptoethanol and incubating at room temperature for 5 minutes. The MeHg treated polyadenylated mRNA was incubated in 200 ul reaction containing 50mM Tris-HCl pH 8.3, 10 mM $MgCl_2$, 20 mM KCl, 5 mM Dithiothreitol, 2 mM each of dATP, dCTP, dGTP and dTTP, 50 µCi $^{32}$PdCTP (specific activity, 800 Ci/mmol), 4 µg oligo(dT) 12–18, (Collaborative Research, Waltham, Mass.) 5 µl RNasin (BIOTECH, Madison, Wis.) and approximately 200 units reverse transcriptase 2O (from Beard, Life Sci., St. Petersburg, Fla.). Incubation was at 42° for 60 minutes.

The reaction was stopped by extraction with phenol and chloroform (1:1), then with an equal volume of chloroform and precipitation by ethanol. The ethanol precipitate was dissolved in 50 µl 10 mM Tris-HCl, 1 mM EDTA, pH=8 and fractionated on a column of Sephadex (Trademark, Pharmacia, Inc., Uppsala, Sweden) G-75 in a 1 ml Falcon (Trademark, Falcon Plastics, Oxnard, Calif.) plastic pipette, using 10 mM Tris-HCl, pH 7.4, and 1 mM EDTA as the running buffer. The leading peak of unexcluded $^{32}$p counts was collected (approximately 300 µl) and adjusted to 0.3M NaOH and 1 mM EDTA and incubated overnight at room temperature. Following neutralization with 5M sodium acetate pH 3.8 to a final pH of approximately 6.0, and ethanol precipitation, the second DNA strand was synthesized in a 50 µl reaction containing the same buffer as described Supra, 500 µM each of dATP, dCTP, dGTP, dTTP, 125 µCi $^{32}$PdCTP (800 Ci/mmole) and 50 units reverse transcriptase. Incubation was at 37° C. for 90 minutes. The reaction products were extracted with phenol/chloroform and passed over a Sephadex G-75 column as described above and the excluded $^{32}$p peak was precipitated with ethanol before proceeding to treatment with $S_1$ nuclease.

After fractionation on Sephadex G-75, the second cDNA strand synthesis was completed using the Klenow fragment of DNA polymerase I (Boehringer-Mannheim) in the presence of 50 mM Tris-HCl, pH 8.0, 7 mm $MgCl_2$ and 1 mM dithiothreitol. The reaction mixture was incubated for 4 hours at 15° C., extracted with phenol-chloroform (1:1) and precipitated with ethanol as described above.

The double stranded cDNA was incubated with 300 units of S1 nuclease (Boehringer-Mannheim, Indianapolis, Ind.) in 24 μl of 0.3 mM NaCl, 30 mM Na acetate, pH 4.5, and 3 mM $ZnCl_2$ at 41° C. for 5 minutes. The reaction was stopped by the addition of EDTA to 10 mM and neutralized with Tris base. The $^{32}$P-labelled cDNA was size fractionated using a column of Sepharose CL-4B (Trademark, Pharmacia, Inc., Uppsala, Sweden) made up in a 1 ml Falcon plastic pipette and run in a buffer of 0.3M NaCl, 10 mM Tris-HCl pH 8.0, 1 mM EDTA. Various size classes of double-stranded cDNA were precipitated with ethanol and then tailed using calf thymus terminal transferase (Enzo Biochem., Inc., New York, N.Y.) in a 100 μl volume for 1 minute at 37° C. in a buffer containing 100 mM K cacodylate, pH 7.6, 1 mM $COCl_2$, 0.1 mM DTT, 0.1 mM dCTP, 4 μCi of $^3$H-dCTP, 24 Ci/mmole), and approximately 20 units terminal transferase/μm ds-cDNA. The reaction was stopped by adjusting the solution to 0.5M NaCl, 10 mM EDTA and incubating at 65° C. for 5 min. 1–5 micrograms of yeast+RNA were added prior to extraction with phenol: chloroform and precipitated with ethanol twice. The tailing react ion is described, generally, by Roychoudhury, R., et al, Nucl. Acids Res., 3, 101 (1976). An alternative procedure, also conducted, is described by Land, H., et al, Nucl. Acids. Res. 9:2251, 1981. Approximately 17 bases were added to the 3' end under these conditions. Plasmid pBR322 cleaved by Pst I endonuclease and tailed with dG residues was obtained from a commercial source, New England Nuclear, Boston, Mass. Equimolar amounts of dC tailed cDNA and dG tailed pBR322 were annealed at a concentration of 1 μg/ml, using sequential 2 hour incubations at 42° C., 30° C., and 14° C. The hybrid plasmid DNA was ethanol-precipitated and then used to transform E. coli RR1 cells to ampicillin resistance. Libraries of single colonies were generated and stored in microtiter dishes at −70° C.

According to the alternative procedure, after 15–30 deoxy C residues have been added to the cDNA and annealing to an equimolar concentration of dG-tailed pBR 322 has taken place (at 250 ng of vector/ml), the annealing mixture was incubated at 68° C. for 5 min, then at 42° C. for two hours, followed by slow cooling to room temperature for 2 hours. The hybrid plasmid DNA was used to transform E. coli RR1 cells to tet-resistance as described by Dagert, M. et al, Gene 6:23, 1979. A library was generated and stored as individual colonies in Luria broth with 15% glycerol in microtiter dishes at −70° C.

A library of (300–2000 bp) cDNA fragments was screened for colonies that expressed protein containing the immunochemically reactive region of the sporozoite surface antigen protein. Forty-eight colonies were grown individually on a petri dish containing S agar (32 g/liter tryptone, 5 g/liter NaCl, 20 g/liter yeast extract, 15 g/liter Difco agar 0.2 g/liter NaOH and 20 mg/liter tetracycline). The plates were flooded with 2 mls of 0.05M Tris-HCl pH 7.5 and 0.5 mg egg-white lysozyme (Sigma, St. Louis, Mo.) and scraped with a sterile spatula into a 15 ml polypropylene tube (Fisher Scientific Supply). After incubation at room temperature for 30 minutes, followed by 60 minutes on ice freeze thawing in 95% ethanol and dry ice (−80° C.) three times, and further incubation at 37° C. for 10 minutes the crude cell extracts were treated with DNAse I (1 mg/ml), 4 mM $CaCl_2$ and 4mM $MgCl_2$ at room temperature for 30 minutes and stored at −70° C. for future use.

The lysates were screened for the presence of any immunochemically reactive protein using P. knowlesi monoclonal antibodies, in a radioimmunoassay. In this method, anti-P. knowlesi monoclonal antibody adsorbed to the well of a microtiter dish was used to affinity purify any immunoreactive protein present in pooled cell lysate. Lysates containing an immunoreactive protein were detected by reacting the washed microtiter wells with a second $^{125}$I-labelled anti-P. knowlesi monoclonal antibody. To do this, microtiter plates were coated with 50 μl anti P. knowlesi monoclonal antibody (50 μg/ml) incubated at 4° C. for 12–17 hours, washed thoroughly with 1% (w/v) BSA-saline solution, and then incubated with 50 ul of the pooled cell extract for 4–17 hours at 4° C. After washing, a second $^{125}$I-labelled anti-P. knowlesi monoclonal antibody was added to each well and incubated 2 hours at room temperature. The washed wells were then tested individually for radioactivity. When a pool of 48 colonies was found to be positive, the original single colonies that made up the pool were screened individually and the immunoreactive clones identified, isolated and genetically purified.

Plasmid DNA was purified from 1 liter of cells containing an immunoreactive clone (plasmid pEG81). The cells were grown at 37° in Luria broth with 15 μg/ml tetracycline to approximately $5\times10^8$/cells per ml and the plasmid DNA amplified by adding 175 μg/ml of chloramphenicol and incubating overnight (Clewell and Helinski, J. Bacteriol. 110, 1135 (1972)). The plasmid DNA was extracted from the cells using sodium dodecyl sulphate (SDS) (Godson and Vapnek, Biochim. Biophys. Acta 299, 516 (1973) and purified using 5–20% (w/v) sucrose density gradients. This yielded 500–1000 μg plasmid RF I DNA. 1 μg of this was used to transform other E. coli cells (HB101) to tetracycline resistance and their ability to express the immunoreactive protein was re-checked.

pEG81 DNA was digested with PSI restriction endonuclease ligated with T4 DNA ligase to 0.5 μg of Pst I-cut cloning/sequencing vector M13mp9 at a 1:1 molar ratio and sequenced using the Sanger dideoxy chain termination method (Sanger and Coulson, supra) with a "universal" synthetic primer 5'-d [GTAAAACGACGGCCAGT]-3' (purchased from PL Biochemicals, Milwaukee, Wis.). The complete nucleotide sequence of this segment of the P. knowlesi CS protein gene that contains the immunoreactive site is shown in FIG. 1.

An unexpected feature of the pEG81 fragment of P. knowlesi DNA is that it consisted entirely of a 36 base pair repeat (8 complete units plus a partial unit on either end). The coding strand and correct reading frame of the nucleotide sequence was established as follows:

(a) The reading frame of the Pst I cleavage site of pBR322 ampicillinase gene and of the M13mp9 β-galactosidase genes are known to be identical (5'X C T G C A G X X 3').

| | Met | Thr | Met | Ile | Thr | Pro | Ser | Leu | Ala | Ala | Gly |
|---|---|---|---|---|---|---|---|---|---|---|---|
| M13mp9 | ATG | ACC | ATG | ATT | ACG | CCA | AGC | TTG | GCT | GCA | GGT |
| | | | | | | | | | | Pst I Cleaving Site | |

Two different M13mp9 recombinants were obtained with the P. knowlesi DNA fragment inserted in opposite orientations. One of the recombinants produced an immunoreactive -galactosidase fusion protein (M13mp9/Pk 11) as measured by the radioimmunoassay described supra, the other clone did not. The sequence of M13mp9/Pk 11 therefore identified the coding strand of the DNA.

(b) The reading frame was also deduced from the fact that 17 dC residues were inserted between the β-gal gene and the *P. knowlesi* gene fragment.

(c) One possible reading frame coded for an alanine-rich peptide. That the epitope probably contained alanine was verified by treating authentic *P. knowlesi* CS surface protein with porcine elastase, known to cleave peptides at alanine residues (Powers, J. C., et al, Biochem, Biophys. Acta, 485: 156–166, (1977). Incubation of an extract of $10^6$ sporozoites with 0.002 units porcine elastase (Worthington Enzymes, infra) in Tris-buffer, 0.05M pH 8.6, for 60 minutes at 37° C., completely abrogated the reactivity of the CS protein with monoclonal antibodies as determined by a two-site immunoradiometric assay described in Example 4. Inactivation of the CS protein by elastase was reversed by the synthetic inhibitor OOC-Ala Ala Pro Ala (Powers, et al supra).

Other possible reading frames coded for peptides which were excluded for various reasons: they were too hydrophobic or they contained several cysteine, lysine and arginine residues. The absence of such amino acid residues had been determined in experiments showing that the epitope was resistant to trypsin after complete reduction of the CS protein. Indeed, after incubation of another aliquot of the same sporozoite extract with 1 mg of TPCK-trypsin (Worthington Enzymes, Freehold, N.J.) at 37° C. for 30 minutes, followed by complete reduction and alkylation, the CS protein reacted fully with the monoclonal antibodies.

The deduced amino acid sequence of the twelve amino acid repeat is as follows based upon translation of the nucleotide sequence in the correct reading frame:

Gln-Ala-Gln-Gly-Asp-Gly-Ala-Asn-Ala-Gly-Gln-Pro (All sequences are expressed from the end nearest NH$_2$-terminus on the left to the end nearest the —COOH terminus on the right.)

The immunoreactive portion of the *P. knowlesi* protein is therefore contained within the 12 amino acid repeat.

To confirm that the foregoing amino acid sequence contains the immunoreactive site, a dodecapeptide (with the same order of amino acids as shown above) and a dimer of the dodecapeptide have been synthesized, using solid phase resin synthesis (Marglin, H. and Merrifield, R. B., Ann. Rev. Biochem. 39:841–866 (1970). Sequence analysis performed by automated Edman degradation confirmed that the peptide had been correctly synthesized. The final proof that this is the correct epitope has been obtained. Rabbits were immunized with the dodecapeptide coupled to a carrier (bovine gamma globulin in complete Freunds adjuvant). Two weeks after the injection, the rabbits were bled and their serum assayed for the presence of antibodies against the dodecapeptide and against extracts of sporozoites. The results showed that the animals produced high titers (greater than 1:1000) of antibodies to the native CS protein present in the parasite extracts.

Once a clone expressing an immunochemically reactive protein has been identified, the inserted cDNA sequence can be employed as a hybridization probe to identify cDNA coding for sporozoite antigen proteins from other Plasmodium species. The cDNA clone can also be used to screen Plasmodium genomic DNA obtained, for example, from merozoites, to detect DNA sequences coding for sporozoite antigen protein. Therefore, once the first cDNA sequence coding for a sporozoite antigen or fragment thereof is cloned, the subsequent isolation and purification of other species cDNAs is substantially simplified.

EXAMPLE 2

Competition between monoclonals for specific antigen

Monoclonal antibodies which bind to distinct areas of an antigen molecule do not interfere with each other; on the other hand, monoclonal antibodies directed against the same or topographically related epitopes or antigenic determinants, will inhibit each other's activity. Thus, it is possible to map the epitopes of an antigen.

The number of epitopes of CS proteins which react with monoclonal antibodies was determined by an immunoradiometric assay performed as follows:

A) Preparation of plates coated with sporozoite extracts.

Sporozoites were purified from salivary glands of infected mosquitoes as described by Yoshida, N. et al, Science 207, 71 (1980). They were suspended in phosphate-buffered saline (PBS) at a concentration of $10^6$/ml and subjected to sonication (100 W for 3 minutes), then further diluted 20-fold in PBS. Then 50 ul of the suspension were delivered to the bottom of wells of Falcon "3911" microtiter plates, manufactured by Falcon Plastics, Oxnard, Calif. These were incubated overnight at 4° C. and washed with PBS. The wells were then carefully washed with Tween-20 Trademark, Atlas Europol SpA, Ternate, Italy, (0.05% v/v) and incubated for 3 hours in PBS-containing 0.5% (w/v) bovine serum albumin (BSA) to saturate the hydrophobic sites of the plastic.

B) Preparation of monoclonal antibodies.

Monoclonal antibodies were raised against different species of sporozoites as described by Yoshida, et al, supra; and Potocnjak, P., et al, J. Exp. Med. 151, 1504 (1980). The antibodies were isolated from ascitic fluid of mice injected with the hybridomas by standard chromatographic procedures (ion exchange chromatography and filtration in Sephadex G-200). The purity of the antibodies was ascertained by SDS-PAGE. The antibodies were then radiolabeled with $^{125}$I using Iodogen (Pierce Chemical Co., Rockford, Ill.) according to the instructions of the manufacturer. The specific activity varied between $10^7$–$3\times10^7$ cpm per µg protein.

C) Titration of monoclonal antibodies.

The minimal concentration of a monoclonal antibody which saturates the antigen sites in the bottom of wells of microtiter plates was determined as follows:

To a series of tubes containing a constant amount (0.5 ng) of radiolabeled monoclonal antibody diluted in PBS-BSA, increasing amounts of cold antibody were added, maintaining a constant total volume. 30 µl aliquots of the various mixtures containing the same number of counts, but different concentrations of antibody, were delivered to the bottom of individual wells of the microtiter plates pre-coated with specific antigen. After incubation for 1 hour at room temperature, the wells were washed with PBS-BSA and counted in a gamma counter. The greatest concentration of monoclonal antibody yielding a maximum of counts bound, represents the saturating dose of monoclonal antibody.

D) Competition between monoclonal antibodies for binding to the antigen

Several monoclonal antibodies were prepared against the CS proteins of *P. knowlesi*. The monoclonal antibodies were labeled with $^{125}$I and the saturating dose determined as described, supra. Then, cross-titrations were performed as follows to determine whether each cold monoclonal antibody interfered with the binding of any other labeled monoclonal antibody to the solid-phase antigen.

To a series of antigen-containing wells, 50 μl of different concentrations of the various cold monoclonals diluted in PBS-BSA were added. The plates were incubated for 1 hour at room temperature. Then, 50 μl of one of the radiolabeled monoclonals (for example, 2G3) at twice the saturating concentration, were added to all the wells. After an additional hour of incubation, the wells were washed and counted. The number of specific counts bound to antigen was calculated as the number of counts bound in wells incubated with 2G3 alone at the saturating dose minus the number of counts bound in wells incubated with 2G3 in the presence of cold 2G3 at a concentration $10^3$ times the saturating dose. The counts which could not be inhibited by the homologous cold antibody represent non-specific binding. From these numbers, the percentages of inhibition of binding of 2G3 by the other monoclonal antibodies were calculated. The titration was repeated for each labeled monoclonal antibody. The results are summarized in Table 1. It can be seen that all monoclonal antibodies to *P. knowlesi* strongly inhibit each other, indicating that they must bind to closely related or identical epitopes.

An identical procedure was followed to study the specificities of the monoclonal antibodies to *P. vivax* and *P. falciparum* (Tables II and III), *P. malariae* and *P. bergghei* (not shown). The overall results demonstrate that there is a single immunodominant region in every CS protein.

EXAMPLE 3

Competition between monoclonal antibodies and polyclonal antisera for sporozoite antigens.

A) Assay for the binding of polyclonal antibodies to sporozoite extracts. The first step of this assay was essentially the same as that described in Example 2; that is, wells of microtiter plates were coated with crude sonicated extracts of sporozoites, washed with Tween-20 and saturated with PBS-BSA. Then, serial dilutions in PBS-BSA of the polyclonal antibodies to the homologous sporozoite species were prepared and aliquots of 30 μl delivered to the bottom of individual microtiter wells. Controls consisted of wells incubated with dilutions of polyclonal antibodies to an unrelated antigen. After an incubation of 4 hours at room temperature, the wells were washed. The presence of antibodies in the wells was detected with a second antibody ($^{125}$I-labeled and affinity-purified) to the immunoglobulin of the appropriate species. For example, in the case of human polyclonal antibodies, the second antibody consisted of 50 μl (μg/ml) of an affinity-purified rabbit anti-human Ig. The rabbit antibodies were poly-specific, reacting with human kappa, gamma and mu chains, and had been preabsorbed with mouse Ig. This absorption was necessary to prevent the interaction of the developing reagent with the mouse monoclonal antibodies used in the inhibition assay described below. When monkey polyclonal antibodies were used, the developing reagent was similarly prepared from a rabbit antiserum to monkey Ig.

B) Inhibition of binding of polyclonal antibodies by monoclonal antibodies

The wells coated with sporozoite extract were first incubated with a purified monoclonal antibody to the repetitive epitope of a CS protein, at saturating levels (see Example 2 for the determination of the saturating dose). After incubation for 1 hour at room temperature, the dilutions of the polyclonal antibodies were added, and the assay proceeded as described above.

Inhibition assays have been performed in the following systems:

1) *P. knowlesi* sporozoite extracts reacting with monkey antisera to X-irradiated *P. knowlesi* sporozoites. Inhibitory monoclonal antibody 2G3 (Cochrane, A. H., et al, Proc. Nat. Acad. Sci. USA 79, 565 (1982)).

2) *P. vivax* sporozoite extracts reacting with serum of humans vaccinated by the bite of X-irradiated *P. vivax*-infected mosquitoes. Inhibitory monoclonal antibody 2F2 (Nardin, E. H. et al, J. Exp. Med. 156:20 (1982)).

3) *P. falciparum* sporozoite extracts reacting with serum of humans vaccinated by the bite of X-irradiated *P. falciparum*-infected mosquitoes. Inhibitory monoclonal antibody 2A10 (Nardin, E. H. et al, supra).

Figure 2B:
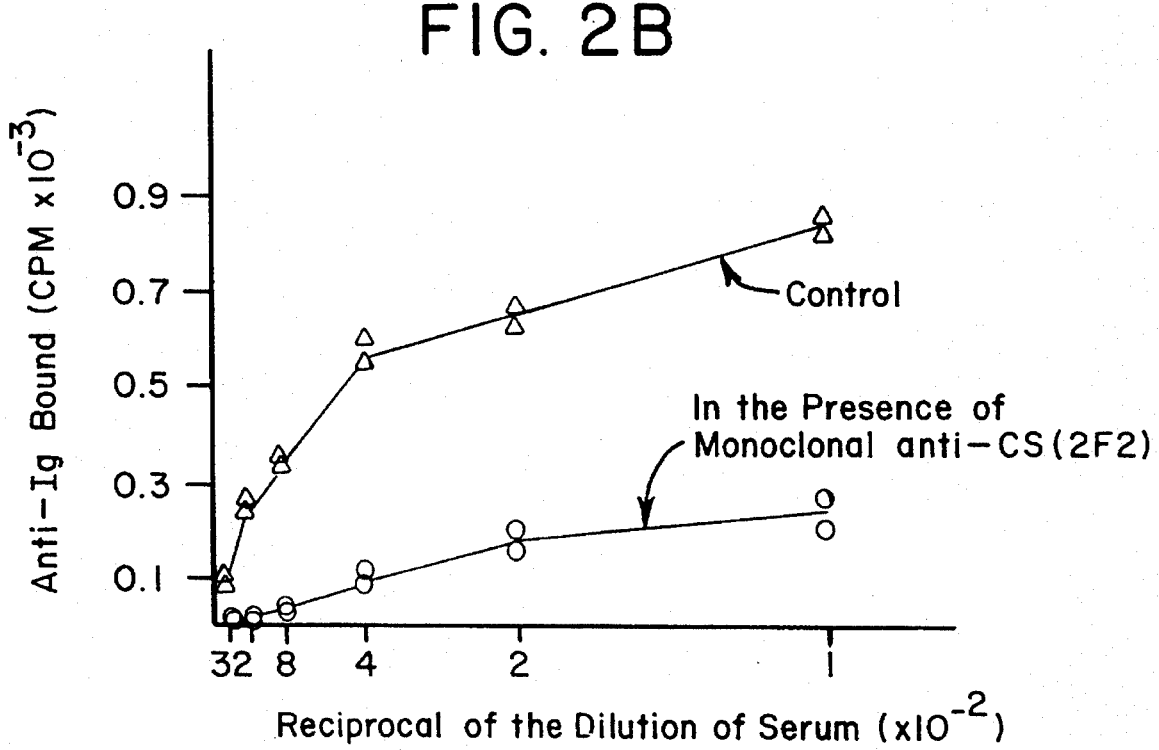
FIG. 2B is a plot showing the inhibitory effect of a monoclonal antibody to a CS protein (monoclonal anti-CS(2F2)) on the binding of polyclonal antibodies to sporozoite extracts.
Figure 2C:
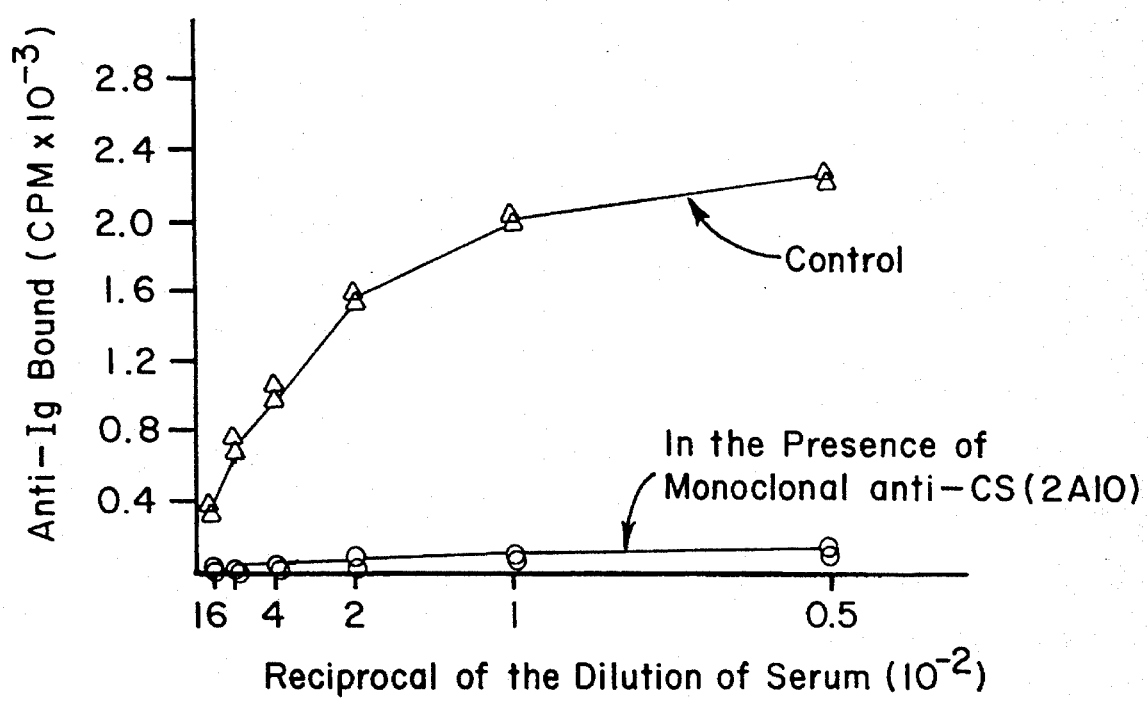
FIG. 2C is a plot showing the inhibitory effect of a monoclonal antibody to a CS protein (monoclonal anti-CS(2A10)) on the binding of polyclonal antibodies to sporozoite extracts.

Typical results of these assays are illustrated in FIG. 2. In every case, the monoclonal antibodies inhibited 70% or more of the interaction between the extracts and the polyclonal antibodies.

Considering that the solid-phase antigen is prepared by sonication of whole sporozoites and probably contains intracellular as well as plasma membrane proteins, these results indicate that a large proportion of the immune response in the polyclonal sera was directed against the repetitive epitope of the immunodominant region of the CS protein (see infra).

EXAMPLE 4

Presence of repetitive epitopes in the immunodominant region of CS proteins from several species of sporozoties.

The experiments in Examples 2 and 3 showed that the CS proteins of four species of Plasmodium contain a single immunodominant region. Shown in this section is the evidence that 1) all immunodominant regions contain a repetitive epitope, and 2) all monoclonals react with a repetitive epitope present in the immunodominant region.

Figure 3A:
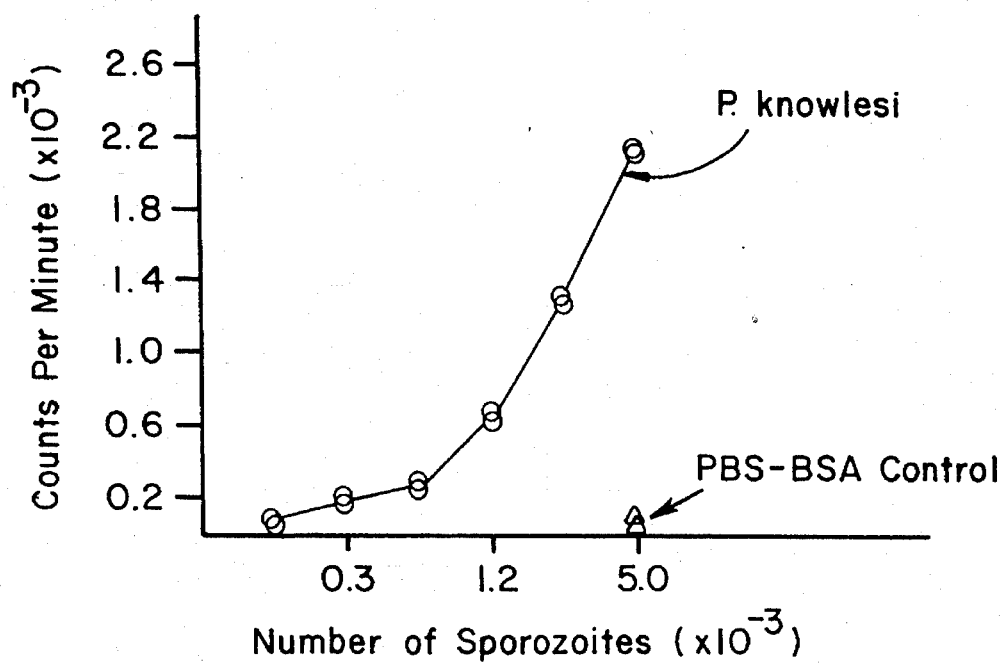
FIG. 3A is a plot showing two-site immunoradiometric assays for detection of sporozoites performed with single monoclonal antibodies to P. knowlesi CS proteins.
Figure 3B:
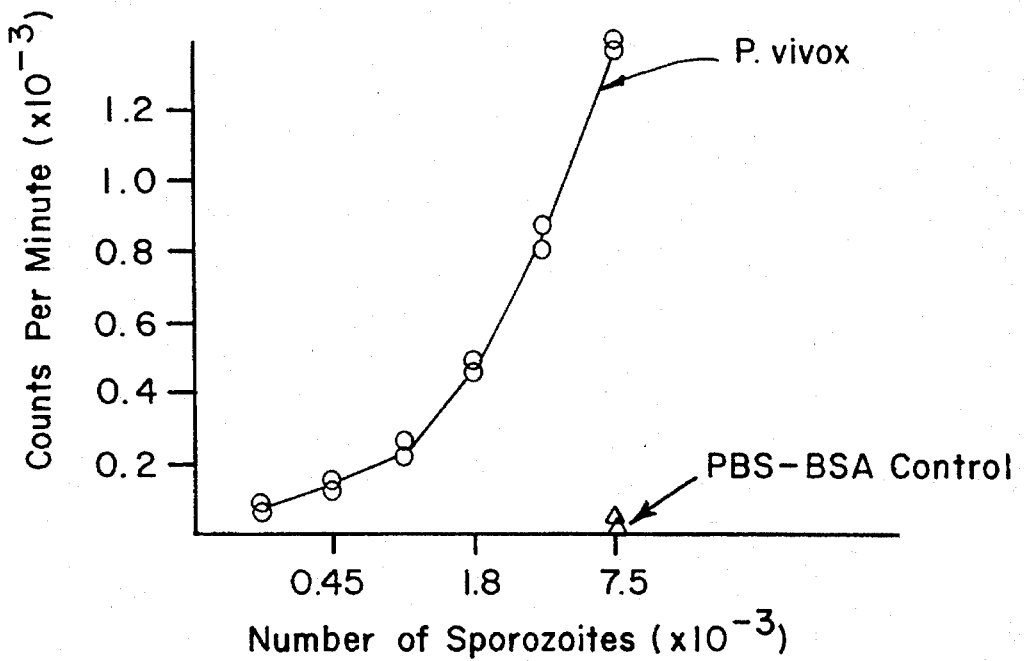
FIG. 3B is a plot showing two-site immunoradiometric assays for detection of sporozoites performed with single monoclonal antibodies to P. vivax CS proteins.
Figure 3C:
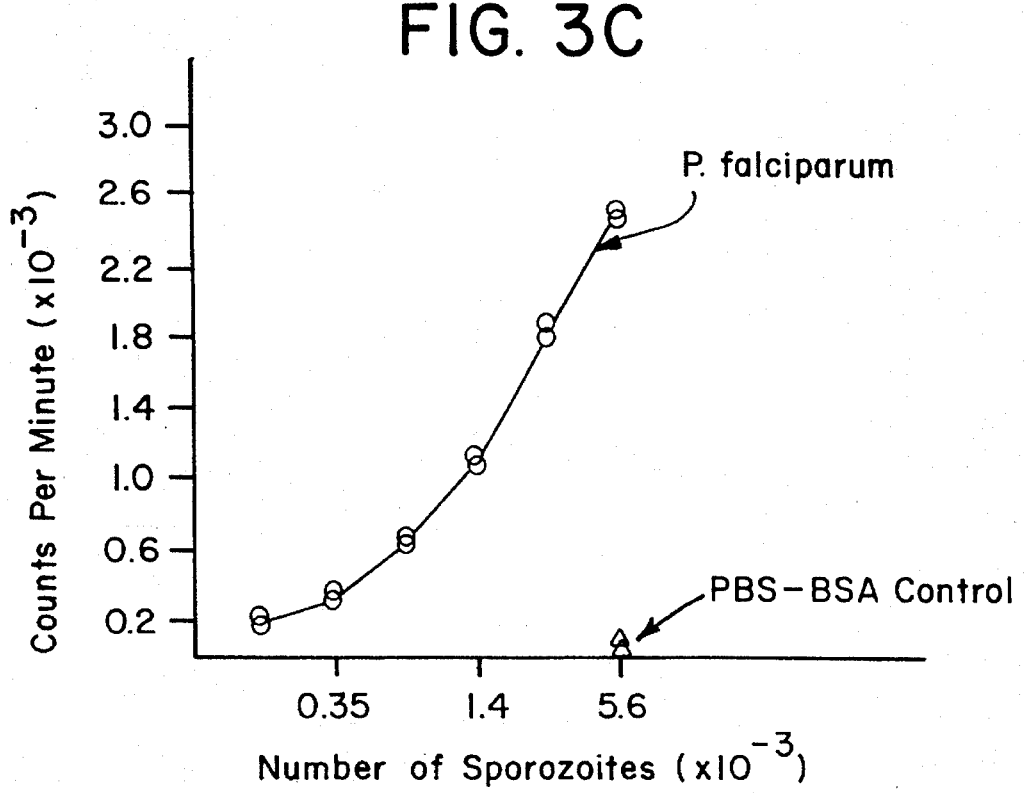
FIG. 3C is a plot showing two-site immunoradiometric assays for detection of sporozoites performed with single monoclonal antibodies to P. falciparum CS proteins.

The presence of repetitive epitopes in CS proteins is based on the observation that two-site immunoradiometric assays to measure CS proteins can be performed with a single monoclonal antibody. This is illustrated in FIG. 3, for the CS proteins of *P. vivax, P. falqiparum,* and *P. knowlesi*. Identical results were obtained with the CS protein of *P. berghei* and the monoclonal 3D11 (not shown) and the CS protein of *P. malariae*. The assays were performed as follows:

Wells of microtiter plates (Falcon 3911) were incubated overnight at 4° C. with 50 μl of a 10 μg/ml solution in PBS of a monoclonal antibody. The wells were washed with PBS and incubated for 2 hours at room temperature with PBS-Tween 20 (0.05% v/v) and for 3 hours at room temperature with PBS-Tween 20-BSA (1% w/v). 30 ul of serial dilutions of extracts of sporozoites were delivered to the bottom of the wells, and the plates incubated overnight in the refrigerator. The extracts had been prepared by treating purified salivary gland sporozoites ($10^7$/ml) with 2% (v/v)NP-40 (Trademark, Particle Data Laboratories, Elmhurst, Ill.) in PBS for 2 hours at room temperature, followed by centrifugation at 100,000 g for 1 hour. The dilutions of the extract were made in PBS-BSA containing 0.1% (v/v) NP-40. After incubation, the wells were washed with PBS-Tween 20-BSA. Then 50 μl (about 5–10 ng) of the same $^{125}$I-labeled monoclonal antibody, diluted in PBS-BSA-Tween 20, were added, and incubation at room temperature proceeded for an additional hour. The wells were washed with PBS-Tween 20-BSA and counted. Controls consisted of wells initially coated with BSA alone. As shown in FIG. 3, specific binding was observed in every instance using the homologous antigen. These experiments demonstrate that the various extracts of sporozoites contain CS proteins which are at least divalent, since they can bind two molecules of a single monoclonal antibody, one of them in solidphase, attached to the plastic, and the other in fluid phase and radiolabeled.

It could be argued, however, that the extracts contained aggregated CS protein. This possibility was excluded by the experiments described below, which show directly that the molecular weight of the divalent or multivalent antigen in the extracts corresponded to that of monomers of the CS proteins.

Extracts were prepared as described above treated with SDS 2% (w/v) –6M urea, and subjected to ultracentrifugation onto 5% (w/v) –20% (w/v) sucrose gradients. The runs were performed in an ultracentrifuge, using a Beckman SW-20 50.1 (Trademark, Beckman Instrument Co., Fullerton, Calif.) rotor at 48,000 rpm for 20 hours. After centrifugation, the bottoms of the tubes were perforated and drops collected in separate tubes. The fractions were analyzed by two methods for the presence of CS protein.

1) Analysis of the fractions by the two-site immunoradiometric assay. This was performed with several monoclonal antibodies for each extract, as described previously in this section. The results of the assays are expressed as number of sporozoite equivalents present in each fraction, as calculated from a standard curve obtained on the same day of the experiment.

2) Analysis of the fractions by inhibition of binding of monoclonals to antigen-coated plates. The gradient fractions were also analyzed by an assay which detects single epitopes on the CS protein. This assay was performed as follows: Antigen-coated plates were prepared, and the minimal saturating dose of radio-labeled monoclonal antibody was determined as described in Example 2. Aliquots of gradient fractions were mixed with the radiolabeled antibody for one hour at room temperature, and then 30 µl of the mixtures were delivered to the wells containing solid-phase antigen. after an additional hour of incubation, the wells were washed and counted. The inhibition of binding is also expressed as number of sporozoite equivalents present in the fraction, as calculated from a standard curve.

Figure 4A:
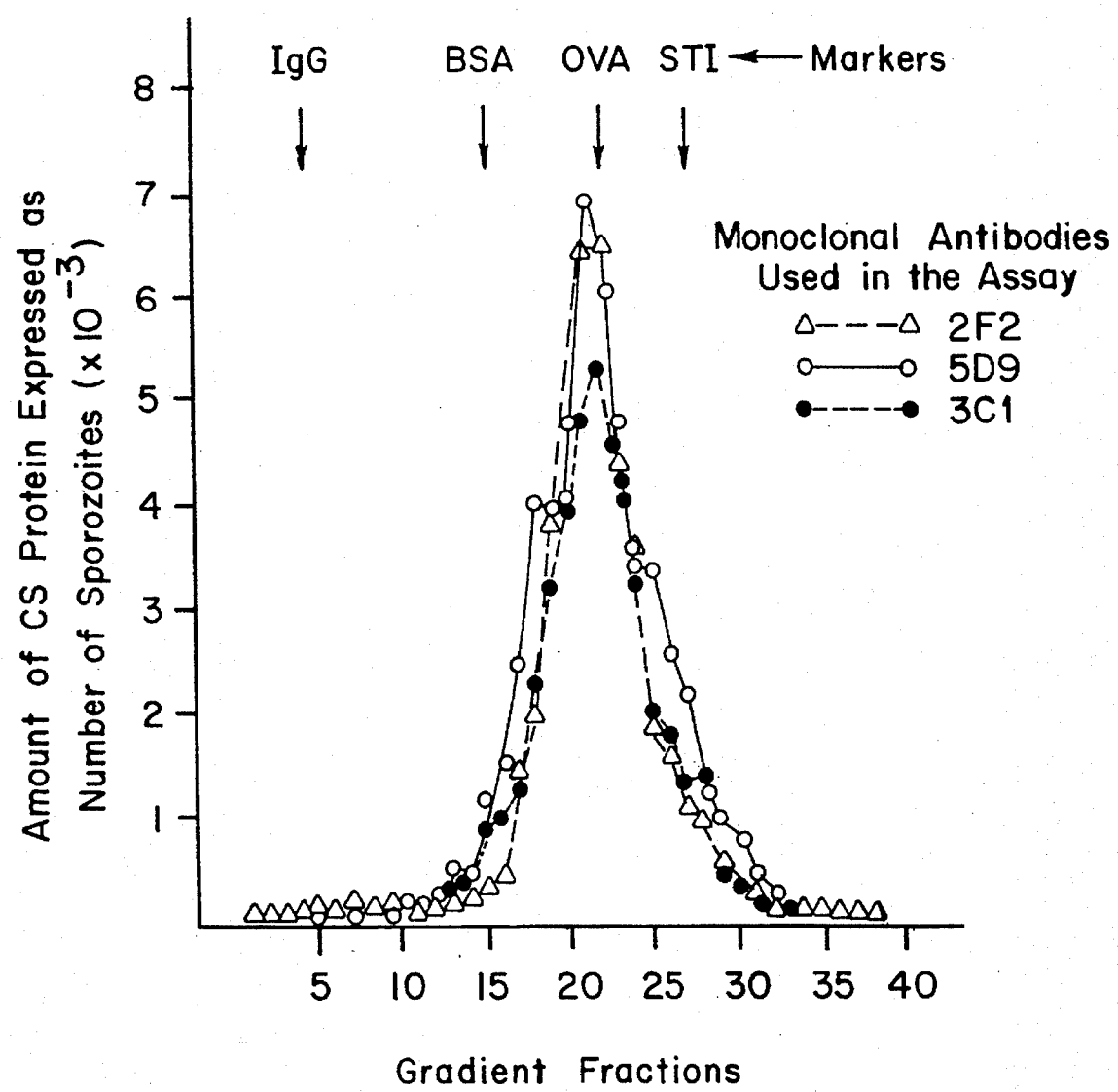
FIG. 4A is a plot showing an immunoradiometric assay of CS protein in gradient fractions after ultracentrifugation of P. vivax sporozoite extracts on sucrose gradients.
Figure 4B:
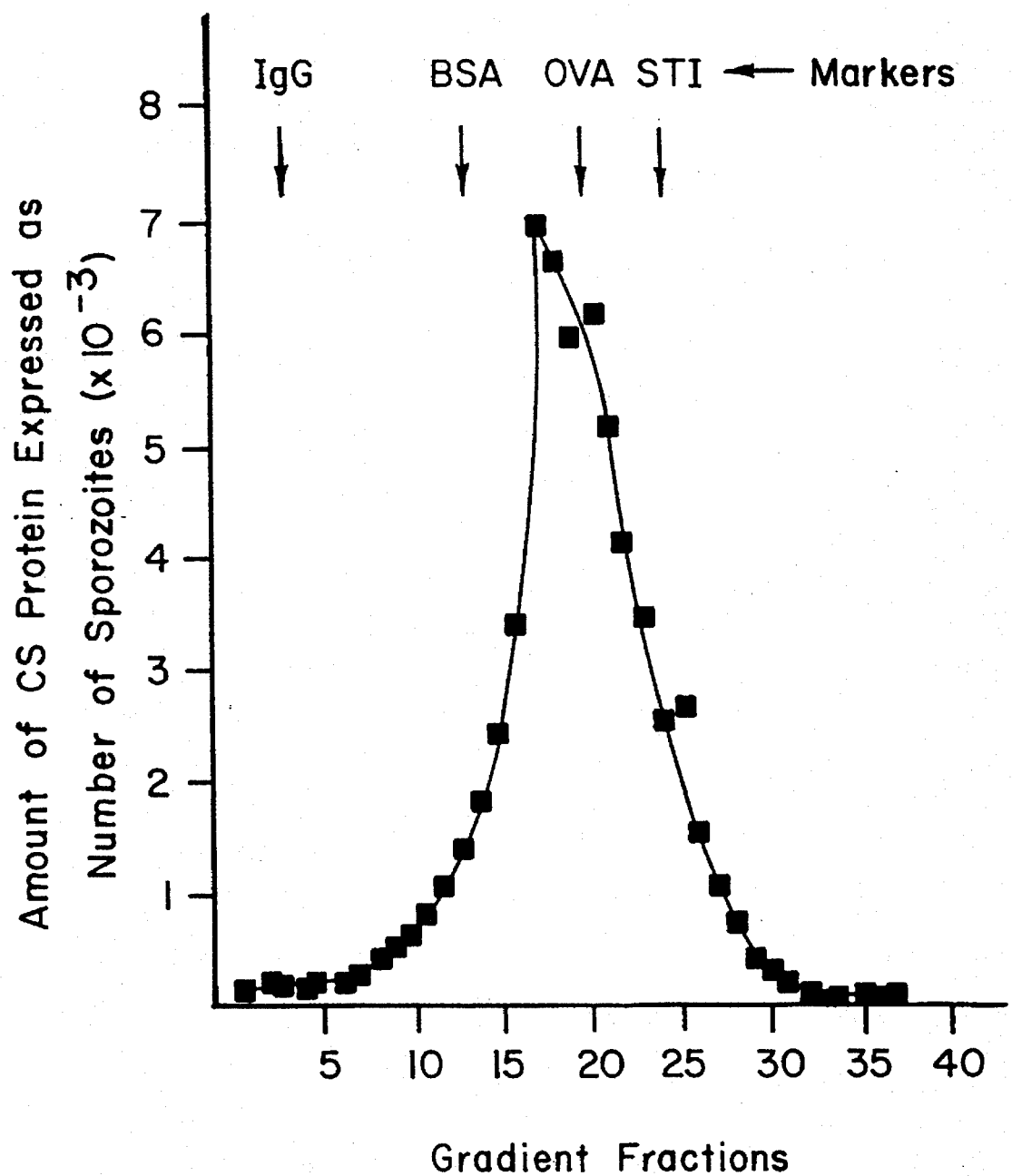
FIG. 4B is a plot showing inhibition by gradient fractions of the binding to antigen-coated plates of a monoclonal antibody to CS protein after ultracentrifugation of P. vivax sporozoite extracts on sucrose gradients.
Figure 5A:
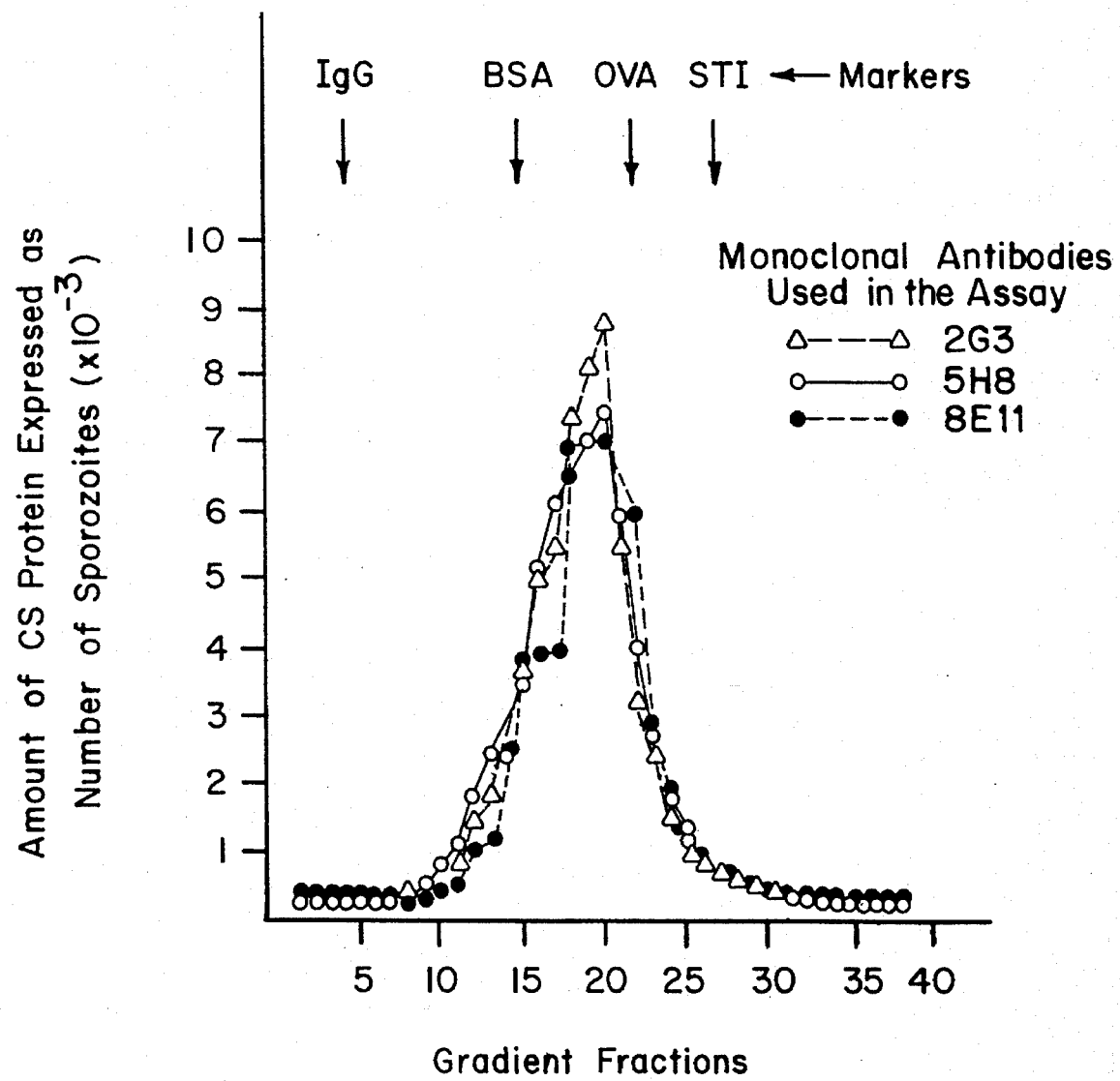
FIG. 5A is a plot showing an immunoradiometric assay of CS protein in
 gradient fractions after ultracentrifugation of P. knowlesi sporozoite extracts on sucrose gradients.
Figure 5B:
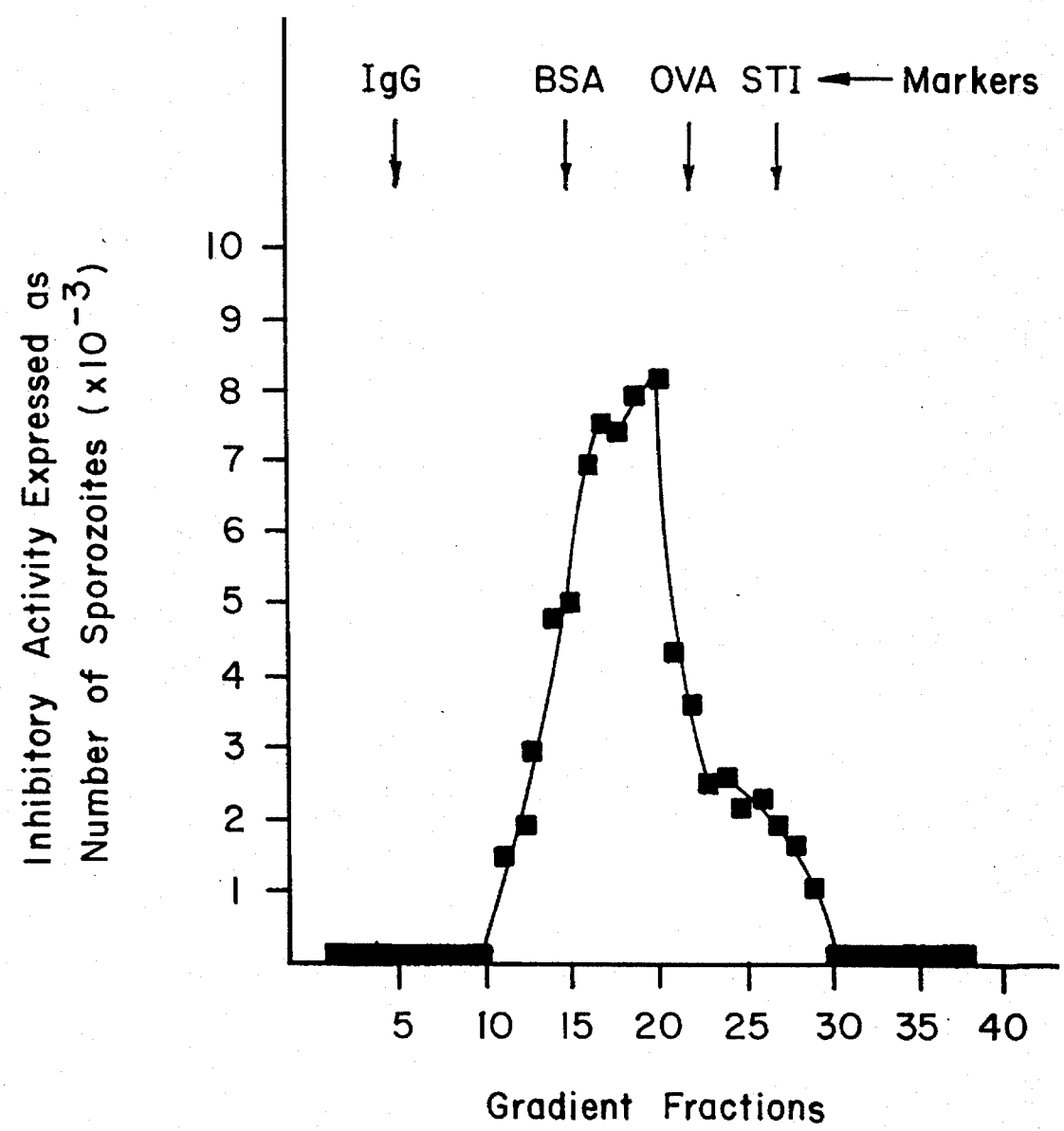
FIG. 5B is a plot showing inhibition by gradient fractions of the binding to antigen-coated plates of a monoclonal antibody to CS protein after ultracentrifugation of P. knowlesi sporozoite extracts on sucrose gradients.

The results of these experiments are summarized in FIGS. 4 and 5, which also show the position in the fractions of marker proteins. The results show that the CS antigen of *P. vivax* and *P. knowlesi* was detected by both assays and sedimented in a single peak between the markers ovalbumin and bovine serum albumin. The amount of CS protein found in this peak represented 95% or more of the original input. Since CS proteins and their precursors have molecular weights between 40,000 and 60,000, these results strongly suggest that the extracts contain mainly or exclusively, monomers of these molecules. Moreover, all monoclonal antibodies tested recognized a repetitive epitope on the CS protein. The simplest explanation for this finding is that all of them react with the same epitope.

In short, the present results and those of the previous examples, demonstrate that the CS proteins of the human malaria parasites *P. vivax*, *P. falciparum* and *P. malariae* contain a single immunodominant region and repetitive epitopes, as in the case of *P. knowlesi*.

EXAMPLE 5

Cross-reactivity between species of sporozoites

The cross-reactions between the monoclonal antibodies to the repetitive epitopes of the CS proteins from various species of Plasmodium were detected by circumsporozoite (CSP) reactions or by the indirect immunofluorescence test. These tests are described in Nardin, E. H., et al, Nature 274, 55 (1978) and Danforth, H. D., et al, J. Parasitol, 64, 1123 (1978), and were performed with monoclonal antibodies.

For example, the CSP reaction is performed by incubation of dilutions of serum in PBS-BSA with purified viable salivary gland sporozoites at room temperature. After 10 minutes or more of incubation, the sporozoites are examined by phase-contrast microscopy. A positive reaction consists of a thread-like precipitate formed at the posterior end of the parasite. The CSP reaction does not occur in the cold, or with formaldehyde-fixed parasites. As demonstrated by Potocnjak, P., et al, supra, the CSP reaction is caused by the cross-linking of the CS protein by antibodies.

The indirect immunofluorescence test is performed with glutaraldehyde-fixed sporozoites. The parasites are treated with 1% (v/v) glutaraldehyde solution in PBS for 30 minutes at 0° C. Then they are washed in PBS, and incubated overnight with 0.1% (w/v) 5 glycine in water. After washing by centrifugation, the resuspended sporozoites are deposited within 10 µl droplets on microscopic slides, at a concentration of $2 \times 10^6$/ml. The droplets are air-dried and kept at $-70°$ C. The assay is performed by incubation of the sporozoites with dilutions of the immune serum for 2 hours at room temperature, followed by washings with PBS, and a new incubation for 2 hours with a second antibody, fluorescein-labeled, directed against the Ig of the first immune serum. The second antibody (for example, rabbitanti-human Ig) can be obtained from a commercial source (Cappel Laboratories, Cochranville, Pa.). After washing, the slides are viewed with a fluorescence-microscope.

Using both procedures, the following cross-reactions were observed between monoclonal antibodies to the repetitive epitopes of the CS protein:

A) anti-*P. knowlesi* reacted with *P. falciparum* and *P. cynomolgi*;

B) anti-*P. cynomologi* reacted with *P. vivax*;

C) anti-*P. nigeriensis* reacted with *P. berghei*. In this case the cross-reactive monoclonal antibodies even neutralized the infectivity of the heterologous species; and D) anti-*P. malariae* reacted with *P. brasilianum*.

EXAMPLE 6

Reactivity of synthetic peptides with monoclonal antibodies to the repetitive epitope of *P. knowlesi*

The two synthetic peptides described in Example 1 were used in these studies. One of them was composed of the 12 amino acid sequence. H$_2$N-GlnAlaGlnGlyAspGlyAlaAsnAlaGlyGlnPro-COOH (12-MER) and the other was a dimer of the same sequence (24-MER). The 24-MER (but not the 12-MER) was directly shown by immunoradiometric assay to contain two epitopes of the CS protein of *P. knowlesi*. The assay was performed as follows:

Wells of microtiter plates (Falcon 3911) were incubated overnight at 4° C. with 50 µl of a 10 µg/ml solution in PBS of the monoclonal 2G3 anti-CS protein of *P. knowlesi*. The wells were washed with PBS and then incubated for 2 hours at room temperature, with PBS-Tween 20 (0.05% (w/v), and then for 3 additional hours with PBS-BSA (1% (w/v). The synthetic peptides were diluted serially in PBS-BSA-Tween 20, and 30 ul aliquots of the dilutions were delivered to the bottom of individual wells. The plates were incubated overnight in the refrigerator, washed with PBS-BSA-Tween 20, and incubated with 5.0 ul (10 ng) of $^{125}$I-labeled monoclonal antibody 2G3 diluted in PBS-BSA-Tween 20 (about 100,000 cpm). Controls consisted of plates coated with a non-relevant monoclonal antibody of the same isotype as 2G3. The results are shown in Table IV. Specific counts were found only in wells incubated with the 24-MER and they were proportional to the dose of peptide added to the well.

No specific counts of the 24-MER were bound to the wells in which the solid-phase antibody was the monoclonal 3D11, which is directed against the CS protein of *P. berghei*.

These results strongly suggest that the 24-MER contains two identical epitopes recognized by the monoclonal 2G3, and that the 12-MER contains either one epitope or none. To distinguish between these possibilities, an assay was conducted to determine the ability of the 12-MER to inhibit the interaction between the CS proteins of *P. knowlesi* and the monoclonal antibody 2G3. The inhibition assay was performed as follows:

Wells of microtiter plates were coated with the monoclonal antibody 2G3 washed with Tween-20, saturated with BSA as described supra. In one series of tubes, the 12-MER was serially diluted in PBS-BSA-Tween 20. In a second series of tubes, an extract of *P. knowlesi* sporozoites (prepared as described by Cochrane, et al, supra) was serially diluted in PBS-BSA-Tween 20. Aliquots of each dilution of sporozoites were mixed with equal volumes of all dilutions of 12-MER. 30 µl of these mixtures were then added to the bottom of the 2G3-coated wells. As positive and negative controls, 30 µl aliquots of sporozoite dilutions mixed with PBS-BSA-Tween 20 were added to other wells which had been precoated with 2G3 or with a non-relevant monoclonal antibody. After overnight incubation in the refrigerator, the wells were washed and 50 µl (10 µg) of $^{125}$I-labeled 2G3 diluted in PBS-BSA-Tween 20 were added. Following an additional incubation at room temperature for 1 hour, the wells were washed and counted in a gamma counter. The results are shown in Table V. The 12-MER inhibited, in a dose-dependent fashion, the interaction of the *P. knowlesi* CS protein with 2G3.

The conclusion drawn from this experiment is that the 12-MER peptide contains an epitope of the CS protein of *P. knowlesi*.

The reactivity of the synthetic peptides was confirmed by radiolabeling the 24-MER and showing that it bound specifically a monoclonal antibody to *P. knowlesi* (5H8). This experiment was performed as follows:

A) Preparation of Sepharose-4B (Trademark, Pharmacia, Inc. Uppsala, Sweden) coupled to the monoclonal antibodies 5H8 and 3D11, directed against the CS proteins of *P. knowlesi* and *P. berghei* respectively.

The antibodies were coupled to CNBr Sepharose beads (Pharmacia Fine Chemicals Uppsala, Sweden) following the instructions of the manufacturer. After coupling, the beads (containing about 10 mg antibody/ml) were treated for 1 hour at room temperature with 0.5% glutaraldehyde (to prevent leakage of the proteins), then with a solution of 10 mg/ml glycine in PBS, and finally resuspended at 20% volume in PBS-BSA (1% (w/v)) Tween 20 (0.05% (v/v)). The Sepharose-coupled monoclonals were designated Sepharose-5H8 and Sepharose-3D11, respectively.

B) Radiolabeling of the 24-MER was performed with $^{125}$I using the Bolton-Hunter reagent (Amersham International Ltd., Amersham, U.K.) according to the instructions of the manufacturer, using 10 µl of a solution of the 24-MER (10 mg/ml) and 0.1 millicuries of the Bolton-Hunter reagent. The peptide was purified after labeling in a Sephadex-G10 column equilibrated in PBS-gelatin (0.2% (w/v)). Presuming that 100% of the peptide was recovered, the specific activity was $10^5$-cpm/µg of protein.

C) Specific binding of the radiolabeled 24-MER to Sepharose-5H8.

Four 200 µl aliquots of the 20% (w/v) suspension of Sepharose-5H8 were added to tubes containing 150 µl of a dilution of the labeled 24-MER in PBS-BSA-Tween 20 (45,000 cpm). To two of the tubes 50 µl of diluent were added. To the other two tubes 50 µl of cold 24-MER (500 ug) diluted in PBS-BSA-Tween 20 were added. The tubes were incubated overnight in the refrigerator. The beads were washed by centrifugation and counted.

As controls, identical mixtures were prepared in tubes containing Sepharose-3D11. The results are shown in Table VI. These results demonstrate that the radiolabeled peptide bound specifically to the monoclonal antibody 5H8 anti-CS protein of *P. knowlesi*. In addition, it appears that the 24-MER may have interacted weakly with the 3D11 antibody. This is not surprising, considering the evidence that all CS proteins are structurally related, and that, in these experiments, the molar ratio of antibody to the ligand peptide was quite high.

EXAMPLE 7

Immunization with the synthetic repeated epitope of *P. knowlesi* (24-MER)

The synthetic 24-MER is synthesized as described in Example 1, except that a cysteine residue is added at the N-terminus. To determine whether the synthesis has been performed correctly, an aliquot is subjected to acid hydrolysis at reduced pressure (6M HCl, 110° C., 72 hours) and its amino acid composition is determined. The peptide is coupled to a carrier protein either keyhole limpet hemocyanin, or tetanus toxoid, through its N terminal cysteine residue, using m-maleimidolbenzoyl-N-hydroxy-succinimide ester (MBS) as the coupling reagent (Ling, F. T., et al, Biochemistry 18, 690 (1979)). This is a bi-functional reagent which under appropriate conditions reacts specifically with the amino group of the carrier on the one hand, and with the thiol group of the peptides, on the other hand.

4 mg of the carrier protein in 0.25 ml of 0.05M PO$_4$ buffer, pH 7.2, is reacted dropwise with 0.7 mg MBS dissolved in dimethyl-formamide, and stirred for 30 min. at room temperature. The product, that is, MB-carrier, is separated from the unreacted chemicals by passage in a Sephadex G-25 column equilibrated in 0.05M PO$_4$ buffer, pH 6.0. The MB-carrier is then reacted with 5 mg of the 24-MER containing cysteine, dissolved in PBS (pH 7.4). The mixture is stirred for 3 hours at room temperature. Coupling efficiency is monitored with radioactive peptide; that is, a trace amount of $^{125}$I-labeled 24-MER is mixed with cold peptide during the synthesis. Dialysis of the conjugate permits evaluation of the proportion of incorporated label. The number of 24-MER groups per 100,000 M. W. carrier was estimated to be about 10–14.

Five rhesus monkeys are immunized with 200 mg of the conjugated protein adsorbed to aluminum hydroxide gel. Their serum is monitored for the presence of antibodies to CS proteins of *P. knowlesi* by the immunoradiometric assay described in Example 3. That is, serum dilutions are incubated with antigen-coated wells of microtiter plates. The presence of monkey antibody bound to the solid-phase antigen is monitored by incubation with $^{125}$I-labeled affinity-purified rabbit-anti-human Ig (which strongly cross-reacts with rhesus monkey Ig).

After 30 days, the serum titers of the monkeys rise to titers of greater than 1/1000. At this time, these monkeys (as well as five other control monkeys injected with non-conjugated carrier protein adsorbed to aluminum hydroxide) are challenged with 2,000 viable *P. knowlesi* sporozoites. The infection is monitored daily for a total of 30 days by microscopic examination of blood smears, starting one week after the inoculation of the parasites. The results show that the five monkeys immunized with the vaccine (conjugated protein) are totally protected; that is, no parasites are found in their blood. In contrast, the control monkeys have trophozoites of *P. knowlesi* in the circulation 7–12 days after challenge.

EXAMPLE 8

Immunization with the synthetic repeated epitopes of *P. vivax* and *P. falciparum*

The synthetic sequences corresponding to the repeated epitopes of *P. vivax* and *P. falciparum* are synthesized essentially as described in Example 1, except that cysteine residues are added at the N-terminals as described in Example 7. To determine whether the synthesis has been performed correctly, aliquots are subjected to acid hydrolysis at reduced pressure (6M HCl, 110° C., 72 hours) and their amino acid composition is determined. The peptides are coupled to a carrier protein either keyhole limpet hemocyanin, or tetanus toxoid, through its N terminal cysteine residue, by using MBS as the coupling reagent, as described in Example 7.

4 mg of the carrier protein in 0.25 ml of 0.05M $PO_4$ buffer, pH 7.2., is reacted dropwise with 0.7 mg MBS dissolved in dimethyl-formamide, and stirred for 30 min. at room temperature. The product, that is, MB-carrier, is separated from the unreacted chemicals by passage in a Sephadex G-25 column equilibrated in 0.05M $PO_4$ buffer, pH 6.0. The MB-carrier is then reacted with 5 mg of each peptide containing cysteine, dissolved in PBS (pH 7.4). The mixture is stirred for 3 hours at room temperature. Coupling efficiency is monitored with radioactive peptide; that is, a trace amount of $^{125}$I-labelled is mixed with cold peptide during the synthesis. Dialysis of the conjugate permits evaluation of the proportion of incorporated label. The number of synthetic peptides per 100,000 M.W. carrier is estimated to be about 10–14.

Five chimpanzees are immunized with 200 μg of each of the conjugated proteins adsorbed to aluminum hydroxide gel. Their serum is monitored for the presence of antibodies to CS proteins of *P. vivax* and *P. falciparum* by the immunoradiometric assay described in Example 3. That is, serum dilutions are incubated with antigen-coated wells of microtiter plates. The presence of chimpanzee antibody bound to the solid-phase antigen is monitored by incubation with $^{125}$I-labeled affinity-purified rabbit-anti-human Ig (which strongly cross-reacts with chimpanzee Ig).

After 30 days, the serum titers of the chimpanzees rise to titers of greater than 1/1000. At this time, these chimpanzees (as well as five other control chimpanzees injected with non-conjugated carrier protein adsorbed to aluminum hydroxide) are challenged with 2,000 viable *P. vivax* sporozoites. The infection is monitored daily for a total of 30 days by microscopic examination of blood smears, starting one week after the inoculation of the parasites. The results show that the five chimpanzees immunized with the vaccine (conjugated protein) are totally protected; that is, no parasites are found in their blood. In contrast, the control chimpanzees have trophozoites of *P. vivax* in the circulation 10–12 days after challenge.

Next, a second challenge with 10,000 *P. falciparum* sporozoites is given to the same chimpanzees. Again the vaccinated apes are protected, while the controls are all infected.

Based upon the close similarities of human and chimpanzee immune responses and on the fact that protective immunity has been obtained in humans by injection of inactivated sporozoites of *P. falciparum* and for *P. vivax*, the results obtained upon immunization of chimpanzees with the described synthetic peptide will also be obtained following similar treatment of human patients.

What is claimed is:

1. An antigen consisting of at least two occurrences of a repeating peptide unit of the immunodominant epitope region of the circumsporozoite surface protein of a parasite of the genus Plasmodium, wherein the antigen is not said surface protein, and is recognized by antibodies that bind to sporozoites of said parasite.

2. The antigen of claim 1, wherein said antigen is chemically synthesized.

3. The antigen of claim 1, wherein said antigen is an expression product of the DNA of a recombinant microorganism.

4. The antigen of claim 1, wherein said antigen comprises at least two successive occurrences of said repeating peptide unit and said parasite of the genus Plasmodium is selected from the group consisting of *P. falciparum, P. vivax, P. knowlesi, P. malariae, P. cynomolgi, P. berghei*, and *P. yoeli nigeriensis*.

5. The antigen of claim 4 wherein said repeating peptide unit is Gln-Ala-Gln-Gly-Asp-Gly-Ala-Asn-Ala-Gly-Gln-Pro.

6. An antigen consisting of at least two successive occurrences of a repeating peptide unit of the immunodominant epitope region of the circumsporozoite surface protein of *Plasmodium falciparum*, wherein the antigen is not said surface protein and is recognized by antibodies that bind to said surface protein.

7. A fusion protein produced by a recombinant microorganism, said protein comprising an antigenic portion consisting of at least two occurrences of a repeating peptide unit of the immunodominant epitope region of the ciroumsporozoite surface protein of a parasite of the genus Plasmodium at the C-terminal of said fusion protein and a portion of a native protein of said recombinant microorganism at the N-terminal of said fusion protein.

8. A vaccine for immunizing a susceptible mammal against malaria comprising as an active ingredient the antigen of any one of the claims 1–4 and 5–6 and a carrier in a physiologically acceptable medium.

9. The vaccine of claim 8 wherein said antigen is adsorbed on or covalently bound to said carrier.

10. The vaccine of claim 9 wherein said carrier is a carrier protein.

11. A fusion protein according to claim 7 wherein said occurrences of said peptide unit are successive, and said parasite of the genus Plasmodium is selected from the group consisting of *P. falciparum, P. vivax, P. knowlesi, P. malariae, P. cynomolgi, P. berghei*, and *P. yoeli nigeriensis*.

12. A fusion protein of any one of claims 7 and 11, wherein said native protein is the expression product of a beta-galactosidase gene.

13. An antigenic amino acid sequence consisting of the immunodominant epitope region of the circumsporozoite surface protein of a parasite of the genus Plasmodium, said region having a plurality of repeating peptide units, and wherein said antigenic sequence is recognized by antibodies that bind to sporozoites of said parasite.

14. An antigenic amino acid sequence consisting of at least two occurrences of a repeating peptide unit of the immunodominant epitope region of the circumsporozoite surface protein of a parasite of the genus Plasmodium, which is recognized by antibodies that bind to sporozobites of said parasite.

15. The repeating epitope peptide unit of the immunodominant epitope region of the circumsporozoite surface protein of a parasite of the genus Plasmodium.

16. An antigenic composition comprising a polypeptide and a carrier, the polypeptide having at least two occurrences of a repeating peptide unit of the immunodominant epitope region of the circumsporozoite surface protein of a parasite of the genus Plasmodium, wherein the polypeptide elicits antibodies which cross-react with the circumsporozoite surface protein, is not a sporozoite polypeptide consisting of Pb-44, derived from *Plasmodium berghei*; Pk-44, derived from *Plasmodium knowlesi*; Pf-44, derived from *Plasmodium falciparum*; and Pv-44, derived from *Plasmodium vivax*.

17. An antigen according to claim 1, wherein the repeating epitope peptide unit is not more than 12 amino acids in length.

* * * * *